US012678222B2

(12) United States Patent (10) Patent No.: US 12,678,222 B2

Nishio et al. (45) Date of Patent: Jul. 14, 2026

(54) PLASMA ABLATION SYSTEM AND PLASMA GUIDE WIRE

(71) Applicant: Asahi Intecc Co., Ltd., Seto (JP)

(72) Inventors: Yotaro Nishio, Seto (JP); Takaaki Magara, Seto (JP); Shumpei Yoshitake, Seto (JP); Shota Mihara, Seto (JP); Kensuke Sakata, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 301 days.

(21) Appl. No.: 18/211,615

(22) Filed: Jun. 20, 2023

(65) Prior Publication Data

US 2023/0329781 A1 Oct. 19, 2023

Related U.S. Application Data

(63) Continuation of application No. PCT/JP2021/045862, filed on Dec. 13, 2021.

(30) Foreign Application Priority Data

Dec. 25, 2020 (JP) ................................. 2020-216726

(51) Int. Cl.
| | |
|---|---|
| *A61B 18/14* | (2006.01) |
| *A61B 18/12* | (2006.01) |
| *A61B 18/00* | (2006.01) |

(52) U.S. Cl.
CPC ...... *A61B 18/1492* (2013.01); *A61B 18/1206* (2013.01); *A61B 2018/00083* (2013.01);
(Continued)

(58) Field of Classification Search
CPC .............. A61B 18/042; A61B 18/1206; A61B 18/1492; A61B 2018/00083;
(Continued)

(56) References Cited

U.S. PATENT DOCUMENTS

| | | | | |
|---|---|---|---|---|
| 4,998,933 A | * | 3/1991 | Eggers | A61B 18/1492 606/41 |
| 5,419,767 A | * | 5/1995 | Eggers | A61M 25/0158 604/114 |

(Continued)

FOREIGN PATENT DOCUMENTS

| | | |
|---|---|---|
| CN | 111918690 A | 11/2020 |
| JP | 2006-517843 A | 8/2006 |

(Continued)

OTHER PUBLICATIONS

International Search Report and Written Opinion mailed on Mar. 8, 2022, received for PCT Application PCT/JP2021/045862, filed on Dec. 13, 2021, 9 pages including English Translation.

*Primary Examiner* — Michael F Peffley
(74) *Attorney, Agent, or Firm* — XSENSUS LLP

(57) ABSTRACT

A plasma ablation system includes a plasma guide wire having a conductive first electrode formed on a distal end portion, a catheter having a conductive second electrode formed on a distal end side and a lumen through which the plasma guide wire is inserted, and a radio frequency (RF) generator electrically connected to each of the plasma guide wire and the catheter to output a high frequency electric power to the first electrode and the second electrode. The plasma guide wire can ablate a living body tissue by discharge between the first electrode and the second electrode, and the RF generator outputs the high frequency electric power that is 50 W or higher and 100 W or lower during discharge and pulse-modulated to have a duty ratio of 7.4% or higher and 40.0% or lower.

20 Claims, 20 Drawing Sheets

(52) U.S. Cl.
CPC ............... *A61B 2018/00577* (2013.01); *A61B 2018/144* (2013.01)

(58) Field of Classification Search
CPC    A61B 2018/00577; A61B 2018/00583; A61B 2018/144
See application file for complete search history.

(56) References Cited

U.S. PATENT DOCUMENTS

| | | | | |
|---|---|---|---|---|
| 5,716,389 | A | * | 2/1998 | Walinsky ................. A61N 1/06 |
| | | | | 600/374 |
| 6,135,998 | A | | 10/2000 | Palanker |
| 6,582,423 | B1 | * | 6/2003 | Thapliyal ........... A61B 18/1492 |
| | | | | 606/41 |
| 6,780,178 | B2 | | 8/2004 | Palanker et al. |
| 9,179,932 | B2 | | 11/2015 | Davies et al. |
| 10,434,289 | B2 | * | 10/2019 | Tanigaki ............... A61M 25/09 |
| 2008/0119846 | A1 | * | 5/2008 | Rioux ............... A61M 25/0194 |
| | | | | 606/41 |
| 2011/0071517 | A1 | | 3/2011 | Konesky et al. |
| 2017/0164995 | A1 | | 6/2017 | Ma et al. |
| 2020/0268442 | A1 | * | 8/2020 | Paamand ........... A61B 18/1492 |
| 2021/0060293 | A1 | | 3/2021 | Hase et al. |

FOREIGN PATENT DOCUMENTS

| | | | |
|---|---|---|---|
| JP | 2018-524132 | A | 8/2018 |
| WO | 2004/073752 | A2 | 9/2004 |
| WO | 2016/196845 | A1 | 12/2016 |
| WO | 2019/189826 | A1 | 10/2019 |
| WO | 2019191538 | A1 | 10/2019 |
| WO | 2020/246037 | A1 | 12/2020 |

* cited by examiner

| PULSE INTERVAL | EFFECTIVENESS |
|:---:|:---:|
| 1 | B |
| 3 | A |
| 10 | A |
| 15 | A |
| 20 | A |
| 23 | A |
| 25 | A |
| 26 | B |

| VOLTAGE [V] | SIZE OF VAPOR LAYER [mm] |
|:---:|:---:|
| 400 | 0.69 |
| 600 | 1.92 |
| 800 | 2.35 |
| 1000 | 3.23 |
| 1200 | 3.82 |

PLASMA ABLATION SYSTEM AND PLASMA GUIDE WIRE

CROSS-REFERENCE TO RELATED APPLICATIONS

This application is a continuation application of International Application No. PCT/JP2021/045862 filed Dec. 13, 2021, which claims the priority of Japanese Patent Application No. 2020-216726 filed on Dec. 25, 2020, the entire contents of both of which are incorporated herein by reference.

TECHNICAL FIELD

The disclosed embodiments relate to a plasma ablation system and a plasma guide wire.

BACKGROUND ART

In recent years, ablation treatments have become known as treatment methods for arrhythmias or the like that cause abnormal beating rhythm of heart. For example, Patent Literatures 1 to 5 disclose devices and systems that can be used in such ablation treatments, in which a living body tissue (part causing arrhythmia) is excised by using a plasma stream.

In the ablation using the plasma stream, energy emitted from an electrode is absorbed by a living body tissue, and the living body tissue at a temperature above a boiling point is ejected as vapor or plasma. It is known that, for that reason, a vapor layer accompanied by a shock wave or cavitation (bubbles generated by a pressure difference in a liquid) is generated around the electrode, causing the surrounding substances to vibrate, during ablation. In this regard, in the devices and systems described in Patent Literatures 1 to 5, an electrode that emits energy is disposed on a highly rigid member such as a puncture device, a probe, a cutting electrode, and a conductive blade, so that a configuration that can withstand vibration during ablation is obtained.

CITATION LIST

Patent Literature

Patent Literature 1: U.S. Pat. No. 9,179,932
Patent Literature 2: JP 2006-517843 W
Patent Literature 3: U.S. Pat. No. 6,135,998
Patent Literature 4: U.S. Pat. No. 6,780,178
Patent Literature 5: JP 2018-524132 W

SUMMARY

Technical Problems

Incidentally, an inside of a vessel is occluded by a lesion, as in chronic total occlusion (CTO), in some cases. In such a case, it is needed to ablate the lesion to facilitate opening of the CTO. However, in the devices and systems described in Patent Literatures 1 to 5, rigidities of members (puncture device, probe, cutting electrode, conductive blade, etc.) equipped with an electrode are higher than that of a guide wire. Thus, there has been a problem that it is undesirable to push the puncture device or the like described in Patent Documents 1 to 5 forward to a lesion in a complicatedly curved blood vessel, from the viewpoint of safety. This problem is common to general devices or systems for ablation treatment because the device is inserted into not only a blood vessel system, but also an organism lumen such as a lymph gland system, a biliary tract system, a urinary tract system, a respiratory tract system, a digestive organ system, a secretory gland, and a genital organ.

The disclosed embodiments have been made in order to solve at least a part of the above-described and other problems, and to improve safety in the plasma ablation system.

Solutions to Problems

The disclosed embodiments have been made in order to solve at least a part of the above-described and other problems and can be embodied as the following aspects.

(1) An aspect of the disclosed embodiments provides a plasma ablation system. The plasma ablation system includes a plasma guide wire having an elongated external shape and including a conductive first electrode formed on a distal end portion, a catheter having an elongated external shape and including a conductive second electrode formed on a distal end side and a lumen through which the plasma guide wire is inserted, and a radio frequency (RF) generator electrically connected to each of the plasma guide wire and the catheter to output a high frequency electric power to the first electrode and the second electrode, in which the plasma guide wire can ablate a living body tissue by discharge between the first electrode and the second electrode, and the RF generator outputs the high frequency electric power that is 50 W or higher and 100 W or lower during discharge and pulse-modulated so as to have a duty ratio of 7.4% or higher and 40.0% or lower.

According to this configuration, the plasma ablation system includes the plasma guide wire having the conductive first electrode formed on the distal end portion, and the catheter having the conductive second electrode formed on the distal end side. Thus, as a result of outputting the high frequency electric power to the first electrode and the second electrode while the plasma guide wire is inserted through the catheter, the living body tissue can be ablated using an energy emitted by the discharge between the first electrode and the second electrode. In view of the above, the present inventors have determined that by having the RF generator output the high frequency electric power that is 50 W or higher and 100 W or lower during discharge and pulse-modulated so as to have a duty ratio of 7.4% or higher and 40.0% or lower. Thus, for example, even when the first electrode is disposed on a guide wire more flexible (lower rigidity) than conventional configurations of a puncture device, a probe, a cutting electrode, a conductive blade, and the like, the vapor layer generated around the first electrode during ablation can be minimized to suppress flip-up on the distal end portion of the plasma guide wire accompanying vibration of the surrounding substances. As a result, this configuration makes it possible to improve safety in the plasma ablation system.

(2) The plasma ablation system according to the above aspect may be configured such that the RF generator outputs the high frequency electric power pulse-modulated so as to have a duty ratio of 9.1% or higher and 13.0% or lower.

According to this configuration, the RF generator outputs the high frequency electric power pulse-modulated so as to have a duty ratio of 9.1% or higher and 13.0% or lower. Thereby, a size and a depth of a hole formed by ablation can be made larger, while minimizing the vapor layer during ablation to suppress flip-up on the distal end portion of the plasma guide wire.

(3) The plasma ablation system according to the above aspects may be configured such that the plasma guide wire has a distal end load of 0.3 gf or higher and 20.0 gf or lower.

According to this configuration, since the plasma guide wire has a distal end load of 0.3 gf or higher and 20.0 gf or lower, the distal end portion of the plasma guide wire can be made flexible to improve safety.

(4) The plasma ablation system according to the above aspects may be configured such that the plasma guide wire includes, in addition to the first electrode, a conductive core shaft having an elongated external shape, a conductive coil body arranged to surround a part of the distal end side of the core shaft, and an insulative covering portion arranged to cover an outer periphery of the coil body, in which the first electrode fixes each distal end of the core shaft, the coil body, and the covering portion.

According to this configuration, since the plasma guide wire includes the conductive coil body arranged to surround a part of the distal end side of the core shaft, a skin effect on the distal end side of the core shaft can be reduced, and the distal end side of the core shaft can be made thinner than the proximal end side. Since the plasma guide wire includes the insulative covering portion arranged to cover the outer periphery of the coil body, safety can be improved. As a result, the distal end side of the plasma guide wire can be made more flexible, and safety of the plasma ablation system can be improved.

(5) The plasma ablation system according to the above aspects may be configured such that the catheter includes, in addition to the second electrode, a conductive proximal end-side electrode formed on the proximal end side of the catheter and electrically connected to the RF generator, and a conductive connection portion that electrically connects the second electrode with the proximal end-side electrode and is embedded in a thicker wall portion of the catheter.

According to this configuration, the catheter includes the connection portion that electrically connects the second electrode formed on the distal end side with the proximal end-side electrode formed on the proximal end side, and is embedded in the thicker wall portion of the catheter. Thereby, it is possible to prevent obstruction of the operation due to the connection portion entangled with the outer peripheral surface of the catheter, and obstruction of the operation due to the connection portion entangled with the plasma guide wire inserted through the catheter, compared to a case where the connection portion is exposed to the outside or inside of the catheter. As a result, the operability of the plasma ablation system can be improved.

(6) The plasma ablation system according to the above aspects may be configured such that the catheter further includes a mesh-shaped reinforcement portion made of mesh-woven strands and embedded in the thicker wall portion of the catheter.

According to this configuration, since the catheter further includes a mesh-shaped reinforcement portion made of mesh-woven strand, deflection of the catheter can be prevented to improve shape retainability of the catheter.

(7) The plasma ablation system according to the above aspects may be configured such that a straight-line distance between the first electrode of the plasma guide wire and the second electrode of the catheter is 10 mm or longer and 50 mm or shorter.

According to this configuration, since the straight-line distance between the first electrode of the plasma guide wire and the second electrode of the catheter is 10 mm or longer and 50 mm or shorter, the depth of the hole formed in the living body tissue by ablation can be within a desirable range.

(8) According to an aspect of the disclosed embodiments, a plasma guide wire is provided. This plasma guide wire includes a conductive core shaft having an elongated external shape, a conductive coil body arranged to surround a part of a distal end side of the core shaft, an insulative covering portion arranged to cover an outer periphery of the coil body, and a conductive first electrode that fixes each distal end of the core shaft, the coil body, and the covering portion. In view of the above, the present inventors have determined that when the plasma guide wire has a distal end load of 0.3 gf or higher and 20.0 gf or lower provides numerous advantages According to this configuration, since, in the plasma guide wire, the skin effect on the distal end side of the core shaft can be reduced by the conductive coil body, the distal end side of the core shaft can be made thinner than the proximal end side, and the distal end side of the plasma guide wire can be made flexible. Also, safety can be improved by the insulative covering portion arranged to cover the outer periphery of the coil body. As a result, this configuration makes it possible to provide a plasma guide wire suitable for ablation using plasma stream.

(9) The plasma guide wire according to the above aspect may be configured such that the plasma guide wire has a preshaped distal end portion.

According to this configuration, since the plasma guide wire has the preshaped distal end portion, an angle between the distal end portion of the plasma guide wire and a living body tissue can be increased compared to a case without preshaping. As a result, a depth of a hole formed on the living body tissue by ablation can be within a desirable range.

The disclosed embodiments can be embodied in various manners, such as a plasma guide wire, an RF generator, a plasma ablation system equipped with a plasma guide wire and an RF generator, a method for manufacturing these devices and systems, a method for controlling an RF generator in outputting a high frequency electric power to these devices and systems, and a computer program.

BRIEF DESCRIPTION OF DRAWINGS

FIG. 2 is an explanatory diagram illustrating a transverse sectional configuration of a catheter taken along line A-A in FIG. 1.

FIG. 6 is an explanatory diagram illustrating pulse modulation in an RF generator.

FIG. 7 is a graph presenting a result of a test on a size of a vapor layer.

FIG. 12 is a graph presenting a result of the evaluation test on the effectiveness of catching the guide wire.

FIG. 15 is an explanatory diagram illustrating a cross-sectional configuration of a plasma guide wire according to the second embodiment.

DETAILED DESCRIPTION

First Embodiment

Figure 1:
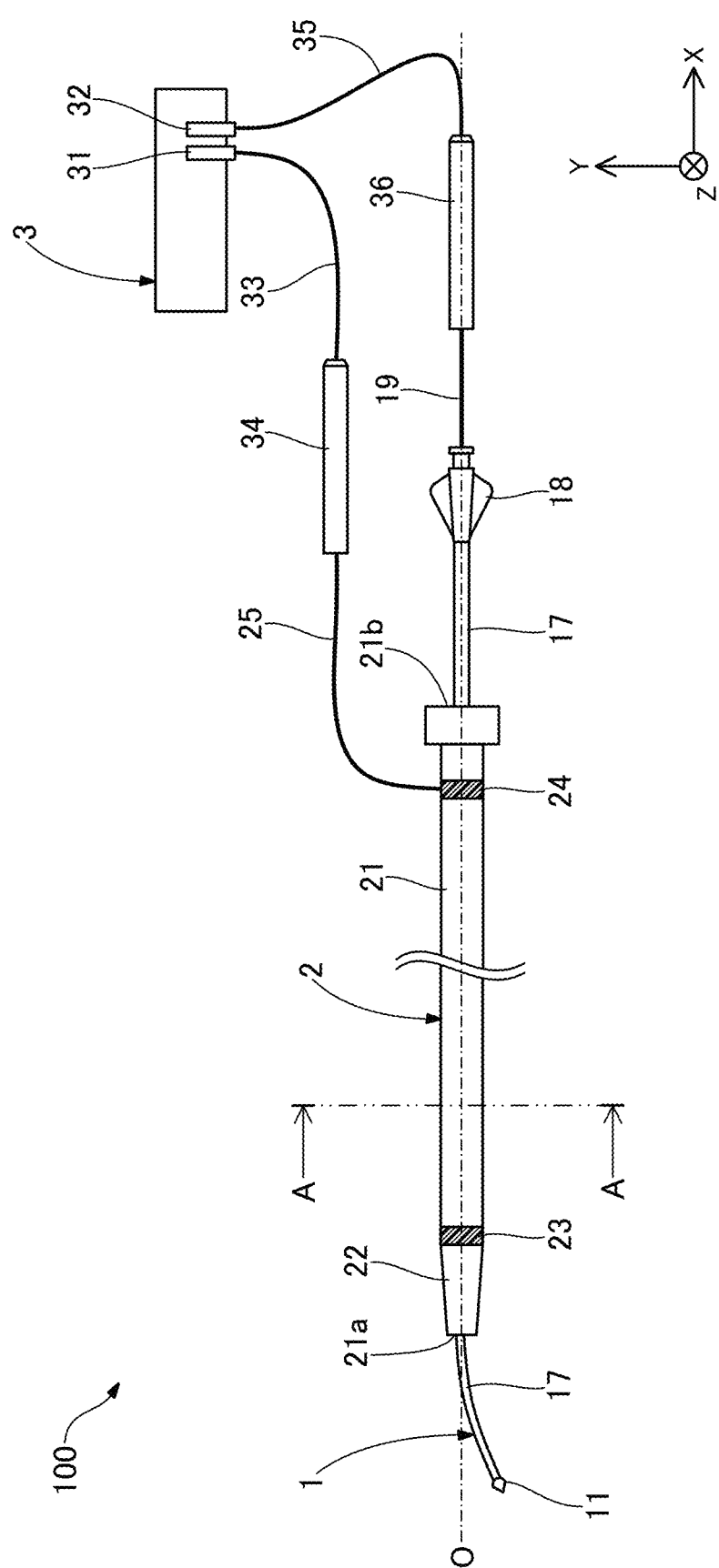
FIG. 1 is a schematic diagram illustrating an overall configuration of a plasma ablation system.

FIG. 1 is a schematic diagram illustrating an overall configuration of a plasma ablation system 100. The plasma ablation system 100 is used for the purpose of opening a chronic total occlusion (CTO), and treating mild to moderate stenosis, significant stenosis, arrhythmia, or the like by ablating a living body tissue. The plasma ablation system 100 includes a plasma guide wire 1, a catheter 2, and an RF generator 3. The plasma ablation system 100 will be explained below in a case of using the plasma ablation system 100 for the purpose of opening a CTO in a blood vessel as an example, but the plasma ablation system 100 can be used so as to be inserted into not only a blood vessel system, but also an organism lumen such as a lymph gland system, a biliary tract system, a urinary tract system, a respiratory tract system, a digestive organ system, a secretory gland, a genital organ, and so forth.

In FIG. 1, an axis that passes through centers of the plasma guide wire 1 and the catheter 2 in the plasma ablation system 100 is represented by an axis line O (dot and dash line). In the example of FIG. 1, the axis line O coincides with each of the axes that passes through the center of the plasma guide wire 1 excluding a part of the distal end side and the center of the catheter 2. However, the axis line O may be inconsistent with, e.g., offset from, each central axis of the plasma guide wire 1 and the catheter 2. FIG. 1 illustrates X-, Y-, and Z-axes orthogonal to each other. The X axis corresponds to a longitudinal direction of the plasma guide wire 1 and the catheter 2, the Y axis corresponds to a height direction of the plasma guide wire 1 and the catheter 2, and the Z axis corresponds to a width direction of the plasma guide wire 1 and the catheter 2. Hereinafter, the left side (−X-axis direction) in FIG. 1 is referred to as a "distal end side" of the plasma guide wire 1, the catheter 2, and each constitution component, and the right side (+X-axis direction) in FIG. 1 is referred to as a "proximal end side" of the plasma guide wire 1, the catheter 2, and each constitution component. One end positioned on the distal end side of the both ends in the longitudinal direction (X-axis direction) is referred to as a "distal end", and the other end positioned on the proximal end side is referred to as a "proximal end". The distal end and the vicinity thereof are referred to as a "distal end portion", and the proximal end and the vicinity thereof are referred to as a "proximal end portion". The distal end side is inserted into an inside of a living body, and the proximal end side is operated by an operator such as a surgeon. These points are also true for figures following FIG. 1.

The plasma guide wire 1 has an elongated external shape and includes a conductive first electrode 11 formed on the distal end portion. The detailed configuration of the plasma guide wire 1 is described below. As illustrated in FIG. 1, the plasma guide wire 1 is to be inserted through a lumen 21L (FIG. 2) of the catheter 2.

The catheter 2 has an elongated external shape and has a conductive second electrode 23 formed on the distal end side and the lumen 21L through which the plasma guide wire 1 is inserted. As illustrated in FIG. 1, the catheter 2 according to the first embodiment includes a shaft portion 21, a distal tip 22, the second electrode 23, a proximal end-side electrode 24, and a cable 25. In FIG. 1, the second electrode 23 and the proximal end-side electrode 24 are hatched with shaded lines to distinguish them from other members.

Figure 2:
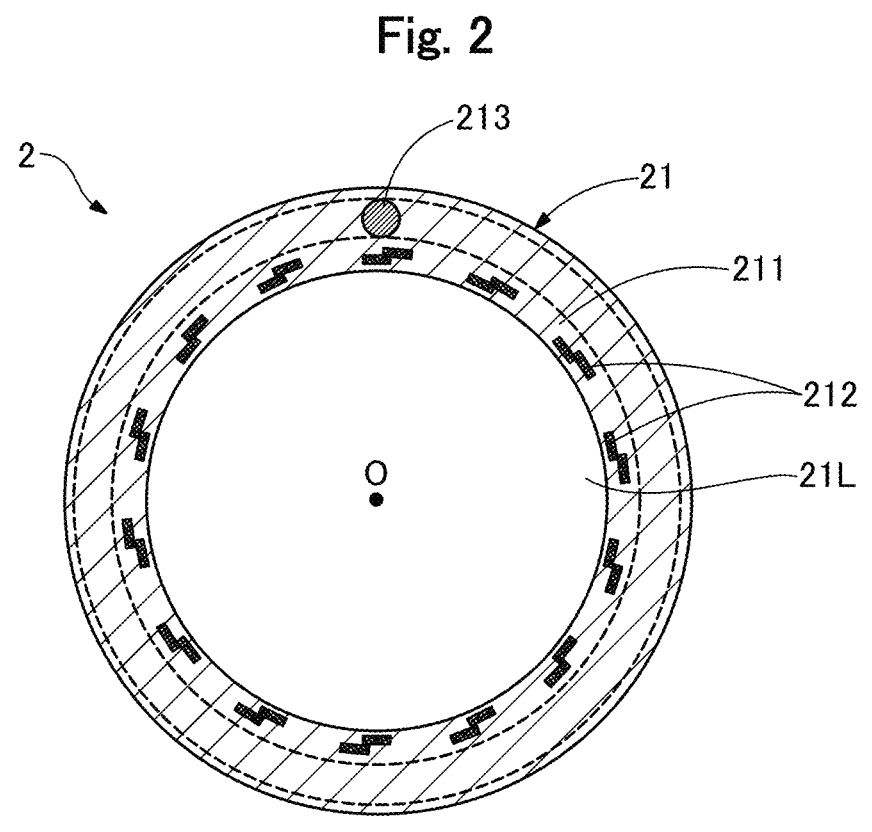

FIG. 2 is an explanatory diagram illustrating a transverse sectional configuration of the catheter 2 taken along line A-A in FIG. 1. As illustrated in FIG. 2, the shaft portion 21 includes a main body portion 211, a reinforcement portion 212, and a connection portion 213.

The main body portion 211 is a member that constitutes the thicker wall portion of the catheter 2 and also insulates between the reinforcement portion 212 and the connection portion 213. The main body portion 211 has an almost hollow-cylindrical shape with openings on both ends. An inner cavity of the main body portion 211 functionally serves as the lumen 21L through which the plasma guide wire 1 is inserted. Hereinafter, the opening on the proximal end side of the main body portion 211 is also referred to as "proximal end opening 21b". An outer diameter and a length of the main body portion 211 can be arbitrarily determined as needed for a particular scenario in which it is to be used. At least one of an outer peripheral surface and an inner peripheral surface of the main body portion 211 may be coated with a hydrophilic or hydrophobic resin. In this case, each of the outer and inner peripheral surfaces of the main body portion 211 may be coated with different types of resins or a same resin.

The reinforcement portion 212 is a member for reinforcing the main body portion 211. The reinforcement portion 212 may have a mesh shape, e.g., made of conductive strands mesh-woven. The reinforcement portion 212 is embedded more inside relative to the connection portion 213 in the main body portion 211. This reinforcement portion 212 allows deflection of the catheter 2 to be suppressed to improve the shape retainability of the catheter 2. The catheter 2 may be configured without the reinforcement portion 212.

The connection portion 213 is conductive and electrically connects the second electrode 23 with the proximal end-side electrode 24. The connection portion 213 may have a coil shape, e.g., made of conductive strands spirally wound along a circumferential direction of the shaft portion 21. The connection portion 213 is embedded more outside relative to the reinforcement portion 212 in the main body portion 211. The distal end portion of the connection portion 213 is electrically connected to the second electrode 23. The proximal end portion of the connection portion 213 is electrically connected to the proximal end-side electrode 24. In other words, the second electrode 23, the proximal end-side electrode 24, and the connection portion 213 constitute one conductor in the catheter 2. The connection portion 213 may be a single-thread coil formed by winding one strand in a single-thread pattern, a multi-thread coil formed by winding a plurality of strands in a multi-thread pattern, a single-thread twisted wire coil formed by winding, in a single-thread pattern, a twisted wire composed of a plurality of strands twisted together, or a multi-thread twisted wire coil formed by winding, in a multi-thread pattern, a plurality of twisted wires composed of a plurality of strands twisted together.

The main body portion 211 may be made of any insulative material, e.g., a polyolefin such as polyethylene, polypropylene, and ethylene-propylene copolymer, a polyester such as polyethylene terephthalate, a thermoplastic resin such as polyvinyl chloride, ethylene-vinyl acetate copolymer, cross-linked ethylene-vinyl acetate copolymer, and polyurethane, a polyamide elastomer, a polyolefin elastomer, a polyurethane elastomer, a silicone rubber, a latex rubber, and the like. The distal tip 22 may be flexible and can be made of e.g., a resin material such as polyurethane and polyurethane elastomer.

Each of the reinforcement portion 212, the connection portion 213, the second electrode 23, and the proximal end-side electrode 24 may be made of any conductive material. Examples of the material include a stainless steel such as SUS316 and SUS304, a nickel-titanium alloy, an alloy containing gold, platinum, or tungsten, which are X-ray opaque materials, and the like. The reinforcement portion 212, the connection portion 213, the second electrode 23, and the proximal end-side electrode 24 may be made of a same material or of different materials.

Referring back to FIG. 1, the distal tip 22 is disposed on the most distal end side of the catheter 2 (i.e. the distal end portion of the catheter 2). The distal tip 22 has an external shape whose diameter is gradually reduced from the proximal end side to the distal end side in order to facilitate advancement of the catheter 2 inside the blood vessel. The distal tip 22 has a through-hole penetrating through the distal tip 22 in the direction of the axis line O. This through-hole communicates with the lumen 21L of the shaft portion 21. Hereinafter, the opening on the distal end side of the through-hole in the distal tip 22 is also referred to as "distal end opening 21a". An outer diameter and a length of the distal tip 22 can be arbitrarily determined for a particular scenario.

The second electrode 23 is conductive and discharges electricity together with the first electrode 11 of the plasma guide wire 1. The second electrode 23 is an annular member arranged to surround the outer peripheral surface of the shaft portion 21 on the distal end of the shaft portion 21. The proximal end-side electrode 24 is conductive and is electrically connected to a first terminal 31 of the RF generator 3 via the cable 25. The proximal end-side electrode 24 is an annular member arranged to surround the outer peripheral surface of the shaft portion 21 on a part of the proximal end side of the shaft portion 21. Lengths of the second electrode 23 and the proximal end-side electrode 24 can be arbitrarily determined. The cable 25 is a conductive electric wire. The cable 25 is connected to the proximal end-side electrode 24.

Figure 3:
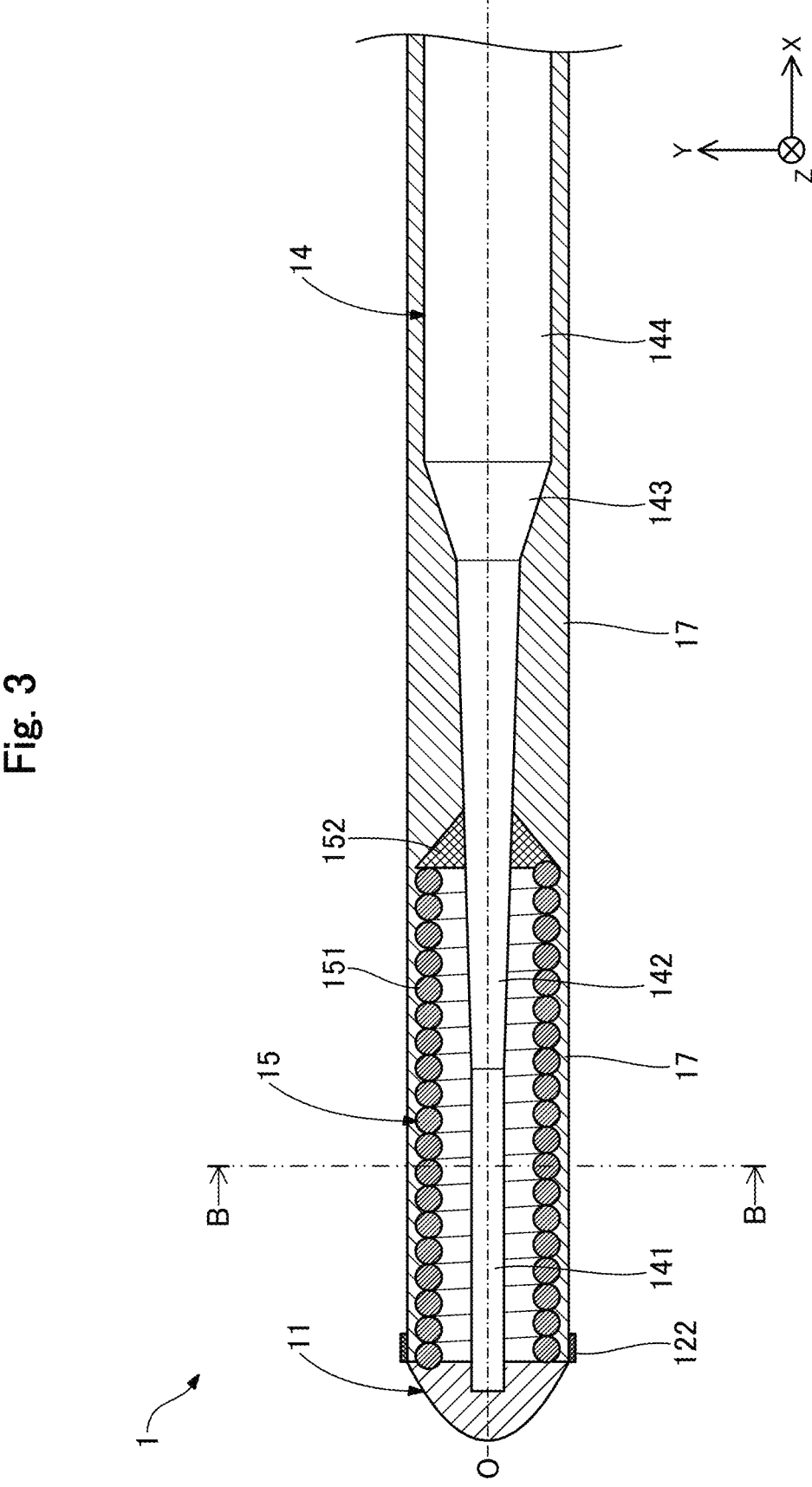
FIG. 3 is an explanatory diagram illustrating a cross-sectional configuration of a plasma guide wire.

FIG. 3 is an explanatory diagram illustrating a cross-sectional configuration of the plasma guide wire 1. As illustrated in FIGS. 1 and 3, the plasma guide wire 1 according to the first embodiment includes the first electrode

11, a core shaft 14, a coil body 15, a covering portion 17, a distal end marker 122, a connector 18 (FIG. 1), and a cable 19 (FIG. 1).

The first electrode 11 is conductive and discharges electricity together with the second electrode 23 of the catheter 2. The first electrode 11 is disposed on the most distal end side of the plasma guide wire 1 (i.e., the distal end portion of the plasma guide wire 1). The first electrode 11 has an external shape with a diameter gradually reduced from the proximal end side to the distal end side to facilitate advancement of the plasma guide wire 1 inside the blood vessel. The first electrode 11 fixes each distal end of the core shaft 14, the covering portion 17, and the coil body 15. The first electrode 11 is joined to each distal end of the core shaft 14 and the coil body 15 by laser welding or the like.

The core shaft 14 is a conductive member constituting the central axis of the plasma guide wire 1. The core shaft 14 has an elongated external shape extending in a longitudinal direction of the plasma guide wire 1. The core shaft 14 may include a small diameter portion 141, a first tapered portion 142, a second tapered portion 143, and a large diameter portion 144 in this order from the distal end to the proximal end. The small diameter portion 141 is a part where an outer diameter of the core shaft 14 is smallest, and has an almost columnar shape with an outer diameter substantially constant from the distal end to the proximal end. The first tapered portion 142 is disposed between the small diameter portion 141 and the second tapered portion 143, and has an external shape with a diameter gradually reduced from the proximal end side to the distal end side. The second tapered portion 143 is between the first tapered portion 142 and the large diameter portion 144, and has an external shape with an outer diameter gradually reduced from the proximal end side to the distal end side at a taper angle different from that of the first tapered portion 142. The large diameter portion 144 is a part where the outer diameter of the core shaft 14 is largest, and has an almost columnar shape with a substantially constant outer diameter from the distal end to the proximal end. The cable 19 (FIG. 1) is electrically connected to the proximal end portion of the large diameter portion 144.

Figure 4:
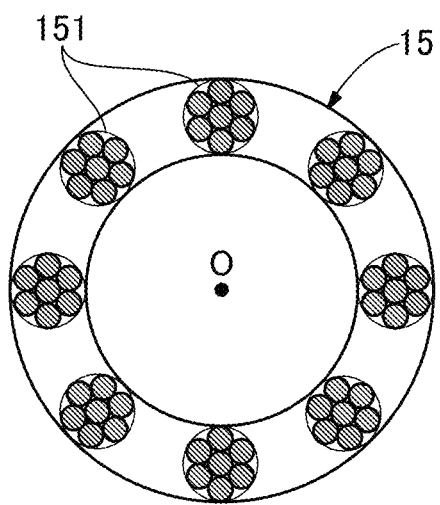
FIG. 4 is an explanatory diagram illustrating a transverse sectional configuration of a coil body taken along line B-B in FIG. 2.

FIG. 4 is an explanatory diagram illustrating a transverse sectional configuration of the coil body 15 taken along line B-B in FIG. 2. The coil body 15 is conductive and arranged to surround a part of the distal end side of the core shaft 14. In an example of FIG. 3, the coil body 15 is arranged to surround each of the whole of the small diameter portion 141 and a part of the distal end-side of the first tapered portion 142. As illustrated in FIG. 4, the coil body 15 is a multi-thread twisted wire coil formed by winding, in a multi-thread pattern, a plurality of twisted wires 151 composed of a plurality of strands twisted together. However, the coil body 15 may be a single-thread coil formed by winding one strand in a single-thread pattern, or a multi-thread coil formed by winding a plurality of strands in a multi-thread pattern, or a single-thread twisted wire coil formed by winding, in a single-thread pattern, a twisted wire composed of a plurality of strands twisted together.

The distal end of the coil body 15 is fixed together with the distal end of the core shaft 14 by the first electrode 11. The proximal end of the coil body 15 is fixed together with a part of the core shaft 14 (specifically, the first tapered portion 142) by a fixation portion 152. The fixation portion 152 is a member that fixes the coil body 15 and the core shaft 14. The fixation portion 152 can be formed by brazing with a hard braze such as silver braze and gold braze. The fixation portion 152 may be formed by welding the coil body 15 with the core shaft 14 by laser welding or the like.

The covering portion 17 is a member that insulates the coil body 15 and a part or the whole of the core shaft 14 from the outside. The covering portion 17 is insulative and is arranged to cover the outer peripheral surface of the coil body 15 and the outer peripheral surface of the core shaft 14 located on a more proximal end side relative to the coil body 15. The covering portion 17 has an almost columnar shape with an outer diameter substantially constant from the distal end to the proximal end. The distal end of the covering portion 17 is fixed together with the distal end of the core shaft 14 by the first electrode 11. The proximal end portion of the covering portion 17 is joined with the proximal end portion of the core shaft 14. The covering portion 17 and the core shaft 14 can be joined using any bonding agent, for example, a metal solder such as silver braze, gold braze, zinc, Sn—Ag alloy, Au—Sn alloy, or an adhesive such as an epoxy adhesive. As illustrated in FIG. 3, a gap may be formed between the covering portion 17 and the core shaft 14. Thus, the covering portion 17 may have an almost hollow-cylindrical shape with an outer diameter substantially constant from the distal end to the proximal end. No gap may be formed between the covering portion 17 and the core shaft 14 such that the inner peripheral surface of the covering portion 17 and the outer peripheral surface of the core shaft 14 we in contact with each other.

The distal end marker 122 is insulative and colored in any color, and functionally serves as a marker for indicating the position of the first electrode 11. The distal end marker 122 is an annular member arranged to surround the outer peripheral surface of the covering portion 17 on the distal end portion of the covering portion 17.

As illustrated in FIG. 1, the connector 18 is located on the most proximal end side of the plasma guide wire 1, and is used by an operator to grasp the plasma guide wire 1. The cable 19 electrically connected to the core shaft 14 extends from the connector 18. The cable 19 is a conductive electric wire.

Herein, the plasma guide wire 1 according to the first embodiment has a distal end load of 0.3 gf or higher and 20.0 gf or lower. The distal end load means the maximum force applied to a lesion when the guide wire is pressed against the lesion. The distal end load of the plasma guide wire 1 can be defined as a weight measured when the distal end of the plasma guide wire 1 is pressed against a precision scale.

The first electrode 11 may be made of any conductive material, such as a chromium-molybdenum steel, a nickel-chromium-molybdenum steel, a stainless steel such as SUS304, and a nickel-titanium alloy. The first electrode 11 may be formed by melting the distal end portion of the core shaft 14 by laser or the like. In this case, the first electrode 11 is formed as a part of the distal end of the core shaft 14 (in other words, a part of the distal end of the core shaft 14 functionally serves as the first electrode 11).

The core shaft 14 may be made of any conductive material, such as a chromium-molybdenum steel, a nickel-chromium-molybdenum steel, a stainless steel such as SUS304, and a nickel-titanium alloy. The coil body 15 may be made of any conductive material, such as a stainless steel such as SUS304, a nickel-titanium alloy, and an alloy containing gold, platinum, or tungsten, which are X-ray opaque materials.

The covering portion 17 and the distal end marker 122 may be made of any insulative material, such as a copolymer of ethylene tetrafluoride and perfluoroalkoxy ethylene (PFA), a polyolefin such as polyethylene, polypropylene, and ethylene-propylene copolymer, a polyester such as polyethylene terephthalate, a thermoplastic resin such as polyvinyl chloride, ethylene-vinyl acetate copolymer, cross-linked ethylene-vinyl acetate copolymer, and polyurethane, a polyamide elastomer, a polyolefin elastomer, a silicone rubber, a latex rubber, and a super engineering plastic such as polyetheretherketone, polyetherimide, polyamideimide, polysulfone, polyimide, polyethersulfone.

Referring again to FIG. 1, the RF generator 3 is a device that outputs a high frequency electric power between the first terminal 31 and a second terminal 32. The first terminal 31 is electrically connected to the catheter 2 via a first cable 33 and a first cable connector 34. The second terminal 32 is electrically connected to the plasma guide wire 1 via a second cable 35 and a second cable connector 36. The first cable 33 and the second cable 35 are conductive electric wires. The first cable connector 34 and the second cable connector 36 are connection terminals for physically and electrically connecting cables to each other.

Thereby, the high frequency electric power output from the first terminal 31 is transmitted to the second electrode 23 through the first cable 33, the first cable connector 34, the cable 25, the proximal end-side electrode 24, and the connection portion 213. Similarly, the high frequency electric power output from the second terminal 32 is transmitted to the first electrode 11 through the second cable 35, the second cable connector 36, the cable 19, and the core shaft 14.

Figure 5A:
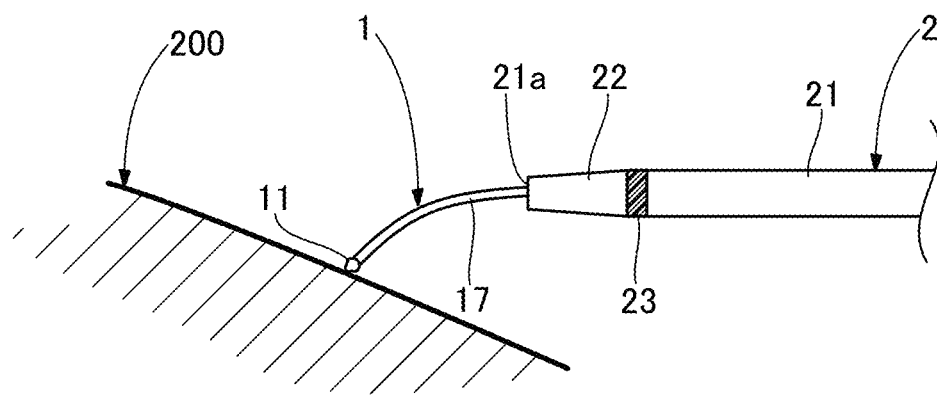
FIGS. 5A to 5C are explanatory diagrams illustrating a manner of ablation.
Figure 5B:
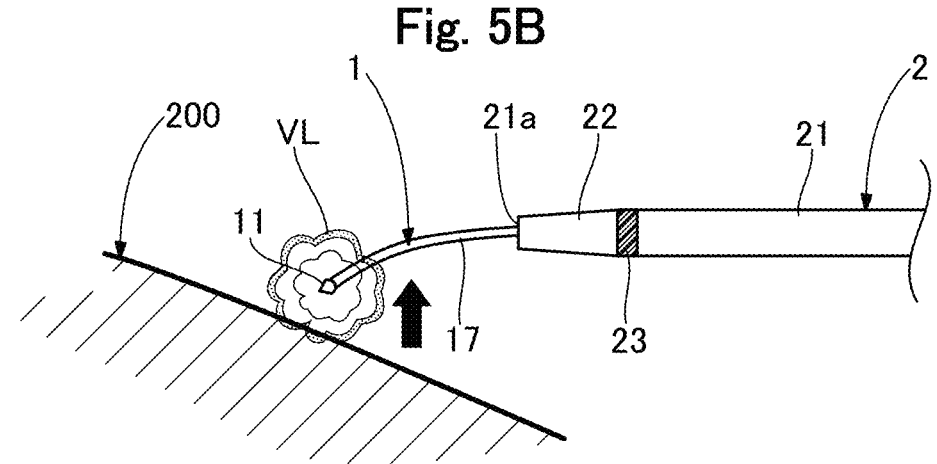
Figure 5C:
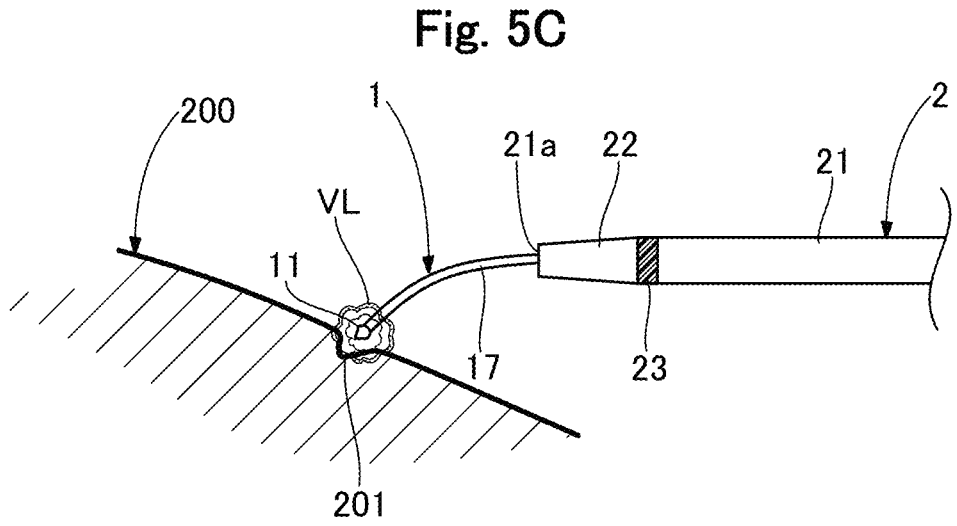

FIGS. 5A to 5C are explanatory diagrams illustrating a manner of ablation. FIG. 5A illustrates a state that the plasma guide wire 1 and the catheter 2 are delivered to the vicinity of the CTO 200. FIG. 5B illustrates a state that ablation is not correctly performed. FIG. 5C illustrates a state that ablation is correctly performed.

First, as illustrated in FIG. 5A, the operator delivers the catheter 2 to the vicinity of the CTO 200, and then outputs the high frequency electric power from the RF generator 3 in a state that the first electrode 11 of the plasma guide wire 1 is protruded from the distal end opening 21a of the catheter 2 and positioned in the vicinity of the CTO 200. Then, the potential difference between the first electrode 11 of the plasma guide wire 1 and the second electrode 23 of the catheter 2 causes a streamer corona discharge between the first electrode 11 and the second electrode 23. This streamer corona discharge makes it possible to ablate the CTO 200 (living body tissue) in the vicinity of the first electrode 11 of the plasma guide wire 1.

In ablation using the plasma stream, energy emitted from the first electrode 11 excites the environment surrounding the living body tissue, so that plasma and vapor are generated, and the energy causes the living body tissue to evaporate. Thereby, during the ablation, a vapor layer accompanied by a shock wave or cavitation (bubbles generated by a pressure difference in a liquid) is generated around the electrode, causing the surrounding substances to vibrate. As mentioned above, the plasma guide wire 1 according to the first embodiment has a distal end load of 0.3 gf or higher and 20.0 gf or lower and is flexible. Thus, when a conventional high frequency electric power is output from the RF generator 3, the distal end portion of the plasma guide wire 1 flips up due to the vibration caused by a vapor layer VL as illustrated in FIG. 5B, and therefore the CTO 200 cannot be correctly ablated.

Thus, in the plasma ablation system 100 according to the first embodiment, the high frequency electric power output from the RF generator 3 is set to the following discharge condition a1 or discharge condition a2.

(a1) A high frequency electric power that is 50 W or higher and 100 W or lower during discharge and pulse-modulated to have a duty ratio of 7.4% or higher and 40.0% or lower.

(a2) A high frequency electric power that is 50 W or higher and 100 W or lower during discharge and pulse-modulated to have a duty ratio of 9.1% or higher and 13.0% or lower.

In such a manner, as illustrated in FIG. 5C, the size of the vapor layer VL can be made smaller than shown in FIG. 5B, and an output power sufficient for ablation can be obtained. As a result, as illustrated in FIG. 5C, flip-up of the distal end portion of the plasma guide wire 1 can be suppressed, and a hole 201 can be formed in the CTO 200.

Figure 6:
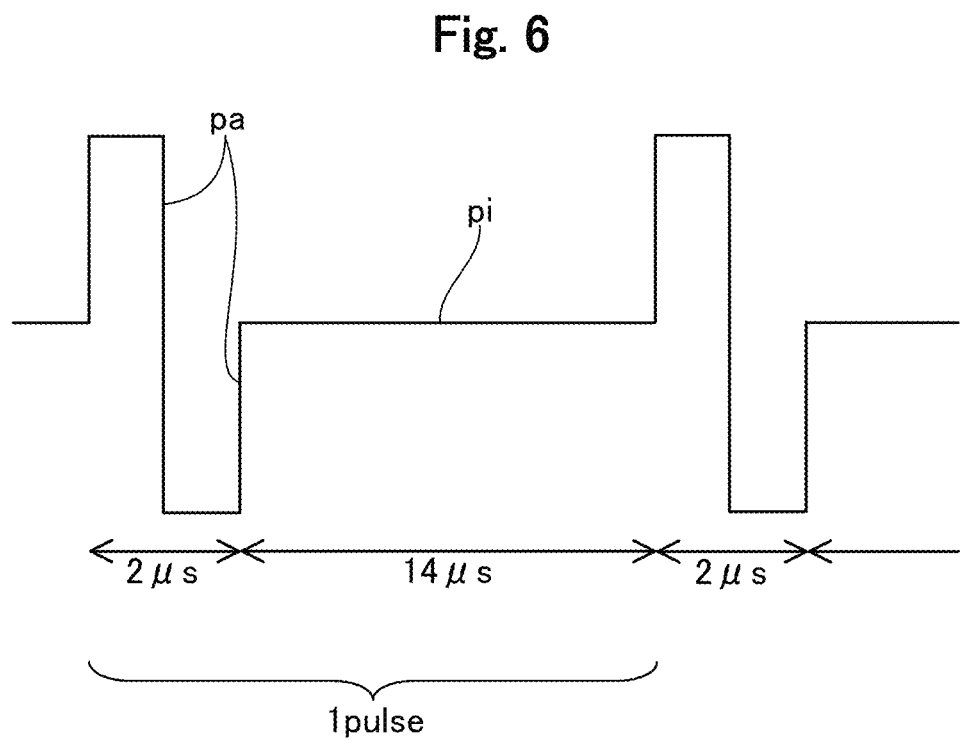

FIG. 6 is an explanatory diagram illustrating pulse modulation in the RF generator 3. FIG. 6 illustrates an example of a case where a pulse with a pulse width pa of 2 μs and a pulse interval pi modulated to 14 μs is defined as one pulse, which is repeated n times (n is a natural number). For the RF generator 3 according to the first embodiment, an alternating current (AC) pulse as illustrated in FIG. 6 is used. The following description explains a reason why the discharge electric power and the duty ratio (pa/(pa+pi)×100) in the aforementioned discharge conditions a1 and a2 in the RF generator 3 are adopted according to the first embodiment.

Figure 7:
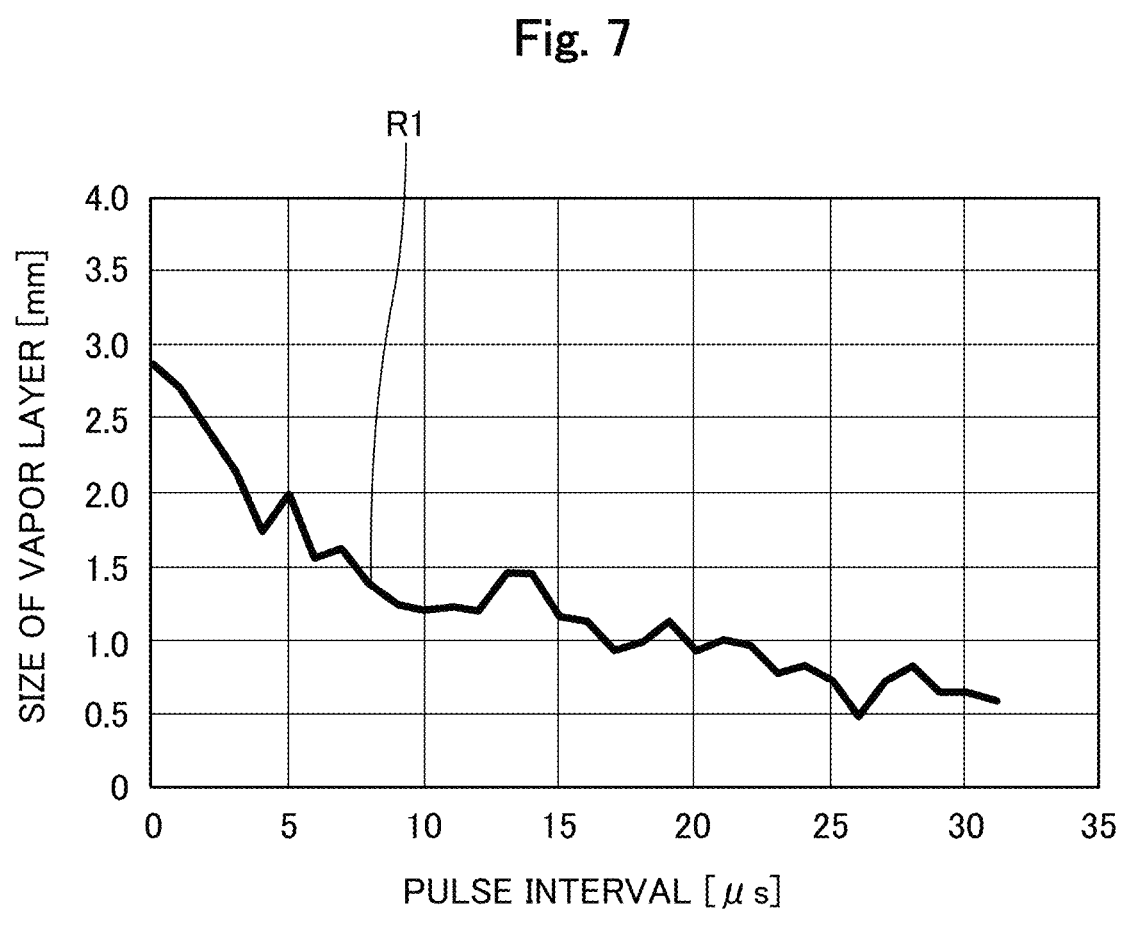

FIG. 7 is a graph presenting a result of a test on the size of the vapor layer. In this test, the discharge conditions of the RF generator 3 were set to discharge conditions b1 to b3 below.

(b1) Discharge voltage: 700 V
(b2) Pulse width pa: 2 μs
(b3) Number of pulses: 200

When the pulse interval pi was changed under the discharge conditions b1 to b3, a state of the first electrode 11 of the plasma guide wire 1 was photographed by a high-speed camera, and the size of the vapor layer VL was measured. As the size of the vapor layer VL, a length of a part where the diameter of the vapor layer VL was largest was measured. In FIG. 7, the value of the pulse interval pi (μs) is on the abscissa, and the value of the vapor layer size (mm) is on the ordinate. FIG. 7 shows that the longer the pulse interval pi is, the smaller the size of the vapor layer VL is, as can be seen from a transition R1 of the vapor layer size.

Figure 8A:
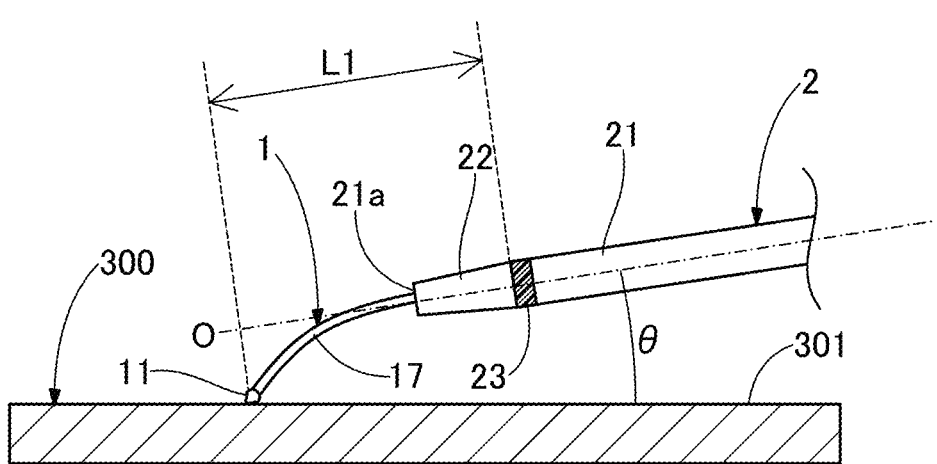
FIGS. 8A and 8B are explanatory diagrams illustrating a method of a test on an ablation effect.
Figure 8B:
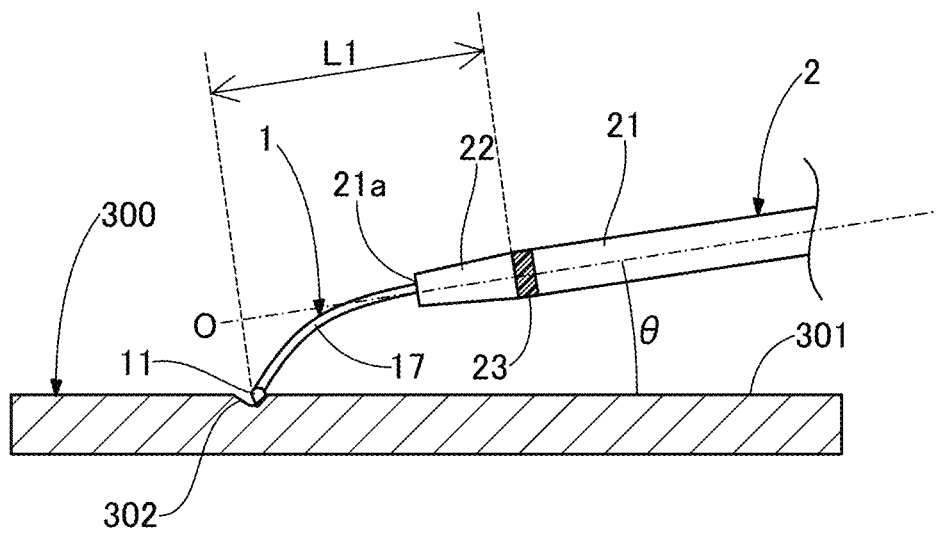
Figure 9A:
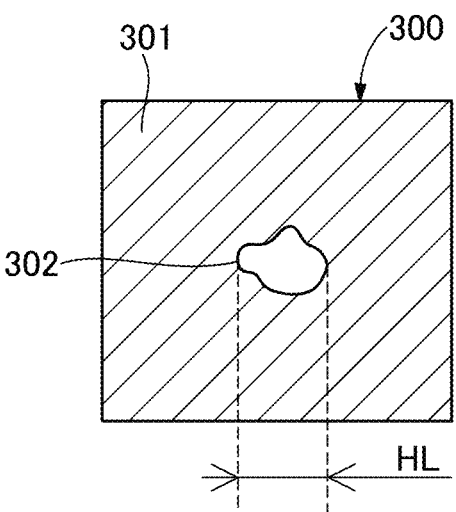
FIGS. 9A and 9B are explanatory diagrams illustrating the method of the test on the ablation effect.
Figure 9B:
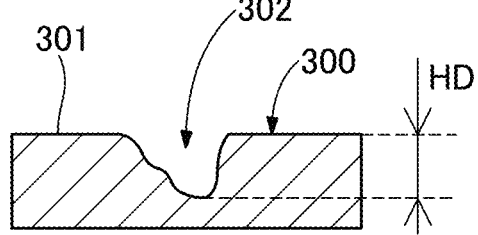

FIGS. 8A, 8B, 9A, and 9B are explanatory diagrams illustrating a method of a test on the ablation effect. FIG. 8A illustrates a state of the plasma guide wire 1 before ablation. FIG. 8B illustrates a state of the plasma guide wire 1 after ablation. FIG. 9A is a diagram illustrating a hole 302 formed on an alternative model 300 viewed from above. FIG. 9B is a cross-sectional view of the hole 302 formed on the alternative model 300.

First, the alternative model 300 of a living body tissue made of a urethane sponge, and physiological saline simulating a body fluid we prepared. The alternative model 300 is immersed in physiological saline. Then, as illustrated in FIG. 8A, the first electrode 11 is brought into contact with a surface 301 of the alternative model 300 while the distal end side of the plasma guide wire 1 is protruded from the distal end opening 21a of the catheter 2. In this experiment, an angle θ between the central axis O of the catheter 2 and the surface 301 of the alternative model 300 is set to 10 degrees. A straight-line distance L1 between the first electrode 11 of the plasma guide wire 1 and the second electrode 23 of the catheter 2 is set to 10 mm. In the example of the figure, the distal end side of the plasma guide wire 1 is preshaped.

In this state, under the aforementioned discharge conditions b1 to b3, a high frequency electric power was output from the RF generator 3 while varying the pulse interval pi, and each hole 302 formed on the alternative model 300 was examined. Specifically, for each of a plurality of holes 302 formed on the alternative model 300, a diameter HL and a depth HD of the hole 302 were measured. As illustrated in FIG. 9A, as the diameter HL of the hole 302, a length of a part where the diameter of the hole 302 formed on the surface 301 was largest was measured. As illustrated in FIG. 9B, as the depth HD of the hole 302, a length from the surface 301 on a part where the depth of the hole 302 was largest was measured.

Figure 10:
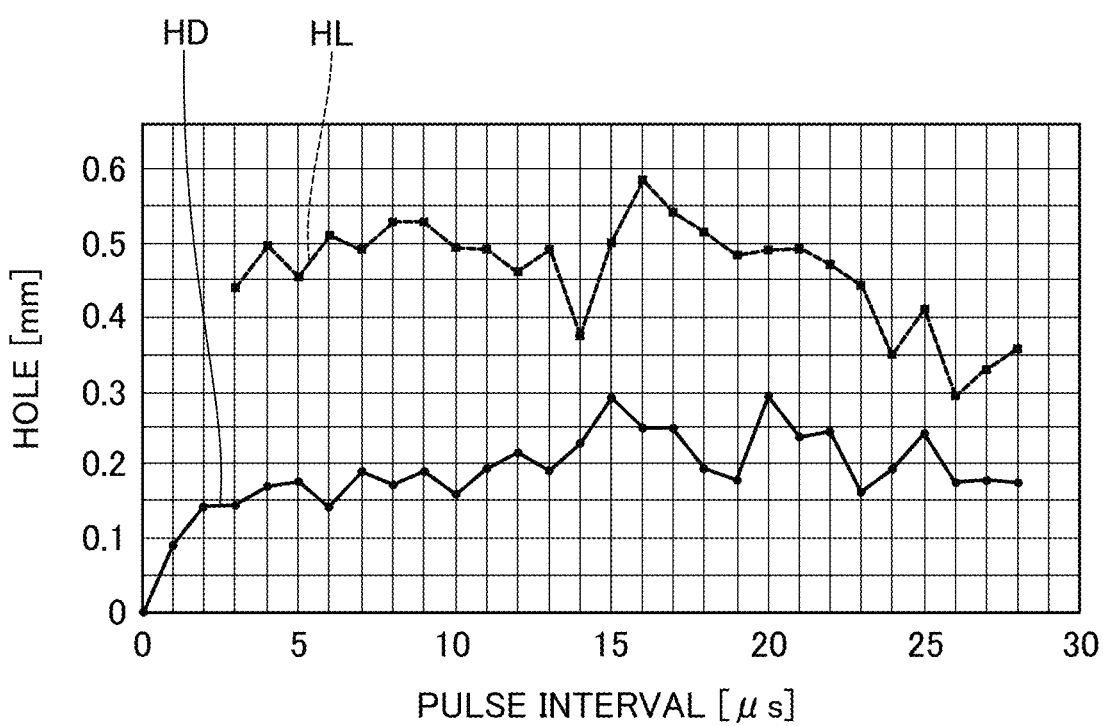
FIG. 10 is a graph presenting a result of the test on the ablation effect.

FIG. 10 is a graph presenting a result of a test on the ablation effect. In FIG. 10, a transition of the diameter HL of the hole 302 as measured by the method described in FIGS. 8A, 8B, 9A, and 9B is represented by a dashed line, and a transition of the depth HD of the hole 302 is represented by a solid line. In FIG. 10, the ordinate represents the measured value (mm) of the hole 302, and the abscissa represents the value (μs) of the pulse interval pi. FIG. 10 shows that, when the pulse interval pi is within a range of 13 μs or more and 25 μs or less, the diameter HL and the depth HD of the hole 302 are relatively larger than those at the other pulse intervals.

Figure 11A:
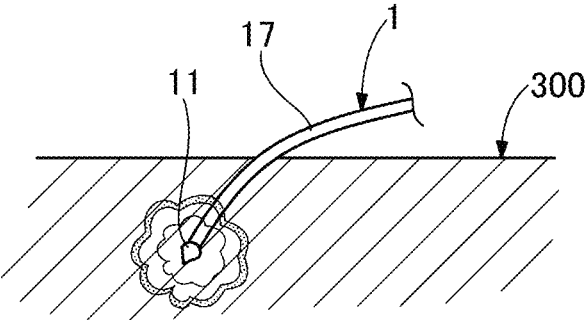
FIGS. 11A to 11C are explanatory diagrams illustrating a method of an evaluation test on an effectiveness of catching the guide wire.
Figure 11B:
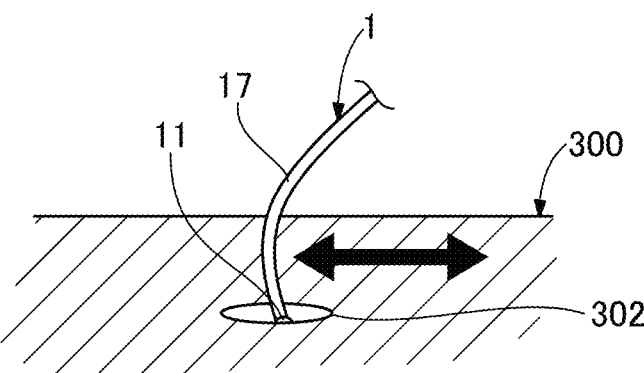
Figure 11C:
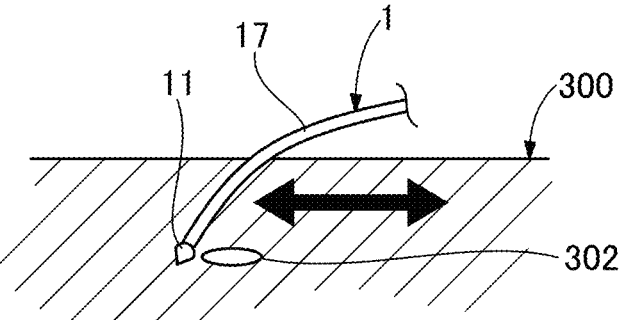

FIGS. 11A, 11B, and 11C are explanatory diagrams illustrating a method of an evaluation test on an effectiveness of catching the guide wire. FIG. 11A illustrates a state of ablation. FIG. 11B illustrates a state that the distal end portion of the plasma guide wire 1 is caught by the hole 302 formed by ablation. FIG. 11C illustrates a state that the distal end portion of the plasma guide wire 1 is not caught by the hole 302 formed by ablation.

First, under the same conditions as described in FIGS. 8A, 8B, 9A, and 9B (specifically, angle θ: 10 degrees, distance L1: 10 mm, discharge conditions b1 to b3), a high frequency electric power was output from the RF generator 3 while varying the pulse interval pi, and the alternative model 300 was ablated. Then, as illustrated in FIGS. 11B and 11C, the plasma guide wire 1 was moved from side to side to evaluate whether the distal end portion of the plasma guide wire 1 was caught by the hole 302 formed on the alternative model 300. Herein, the plasma guide wire 1 inserted into the blood vessel may be affected by the blood flow, fine vibration of hands, or the like and therefore move on the distal end portion as illustrated in FIGS. 11B and 11C. In such a case, if the distal end portion of the plasma guide wire 1 is caught by the hole 302, displacement of the distal end portion is suppressed to facilitate opening of the CTO 200. On the other hand, if the distal end portion of the plasma guide wire 1 is not caught by the hole 302, the distal end portion is displaced, and it takes labor and time to open the CTO 200. Thus, the hole 302 formed by ablation is to have a size and depth enough to catch the distal end portion of the plasma guide wire 1 as illustrated in FIG. 11B.

FIG. 12 is a graph presenting a result of the evaluation test on the effectiveness of catching the guide wire. FIG. 12 presents a result of the effectiveness evaluation for each pulse interval pi, in which a case where the distal and portion of the plasma guide wire 1 was caught is rated as "A", or a case where the distal end portion of the plasma guide wire 1 was not caught is rated as "B". FIG. 12 shows that, when the pulse interval pi is within a range of 3 μs or more and 25 μs or less, the guide wire 1 is caught to facilitate the opening of the CTO 200 even if the angle between the catheter 2 and the alternative model 300 is shallow, e.g., the angle θ is 10 degrees.

Figure 13:
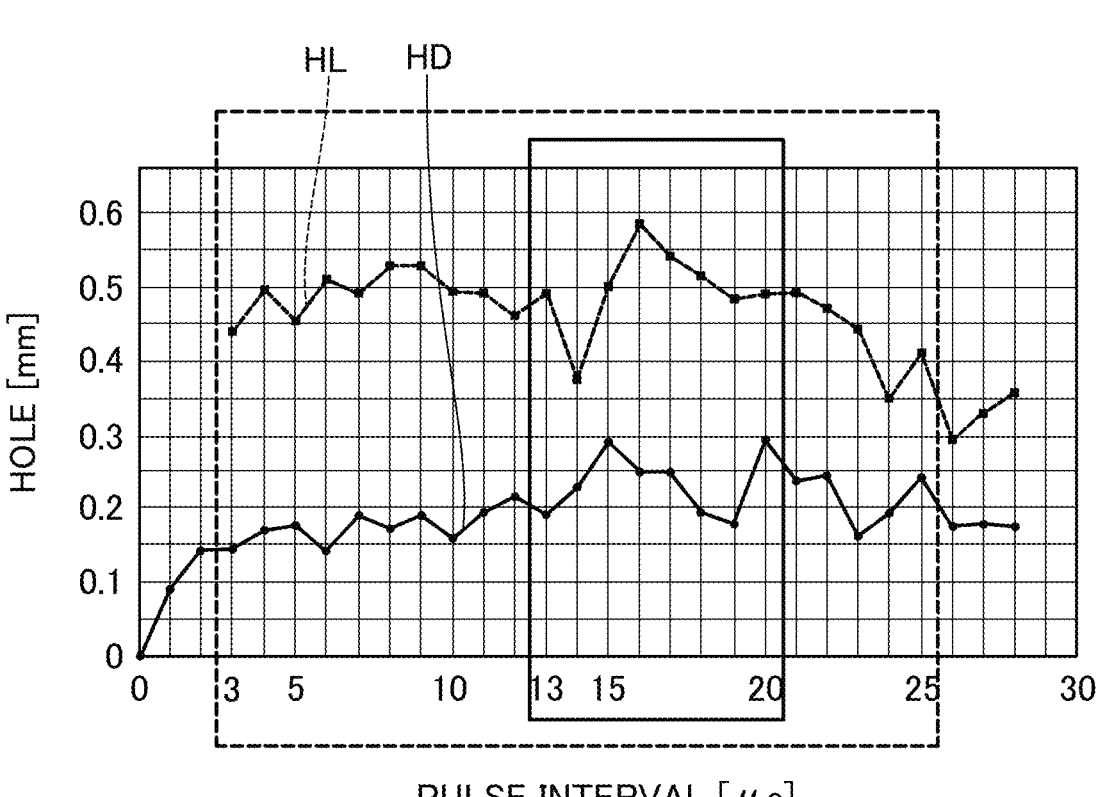
FIG. 13 is an explanatory diagram presenting a range of a pulse interval based on the results of the test on the ablation effect and the evaluation test on the effectiveness of catching the guide wire.

FIG. 13 is an explanatory diagram presenting a range of a pulse interval based on the results of the test on the ablation effect and of the evaluation test on the effectiveness of catching the guide wire. The result of the evaluation test on the effectiveness of catching the guide wire shows that the effect can be obtained when the pulse interval pi is within a range of 3 μs or more and 25 μs or less (FIG. 13: within the dashed line box). Furthermore, from a balance between the diameter HL and the depth HD of the hole 302 formed by ablation, it is found that when the pulse interval pi is within a range of 13 μs or more and 20 μs or less (FIG. 13: within the solid line box), the effectiveness is particularly high. Herein, the duty ratio is determined by dividing the pulse width pa by the total of the pulse width pa and the pulse interval pi and multiplying this quotient by $100(pa/(pa+pi)\times 100)$. Consequently, it can be seen that, under the discharge condition for the RF generator 3, the effect can be obtained when the duty ratio is 7.4% or higher and 40.0% or lower (FIG. 13: within the dashed line box, discharge condition a1). Also, it is found that, under the discharge condition for the RF generator 3, the effectiveness is particularly high when the duty ratio is 9.1% or higher and 13.0% or lower (FIG. 13: within the solid line box, discharge condition a2).

Figures 14A, 14B:
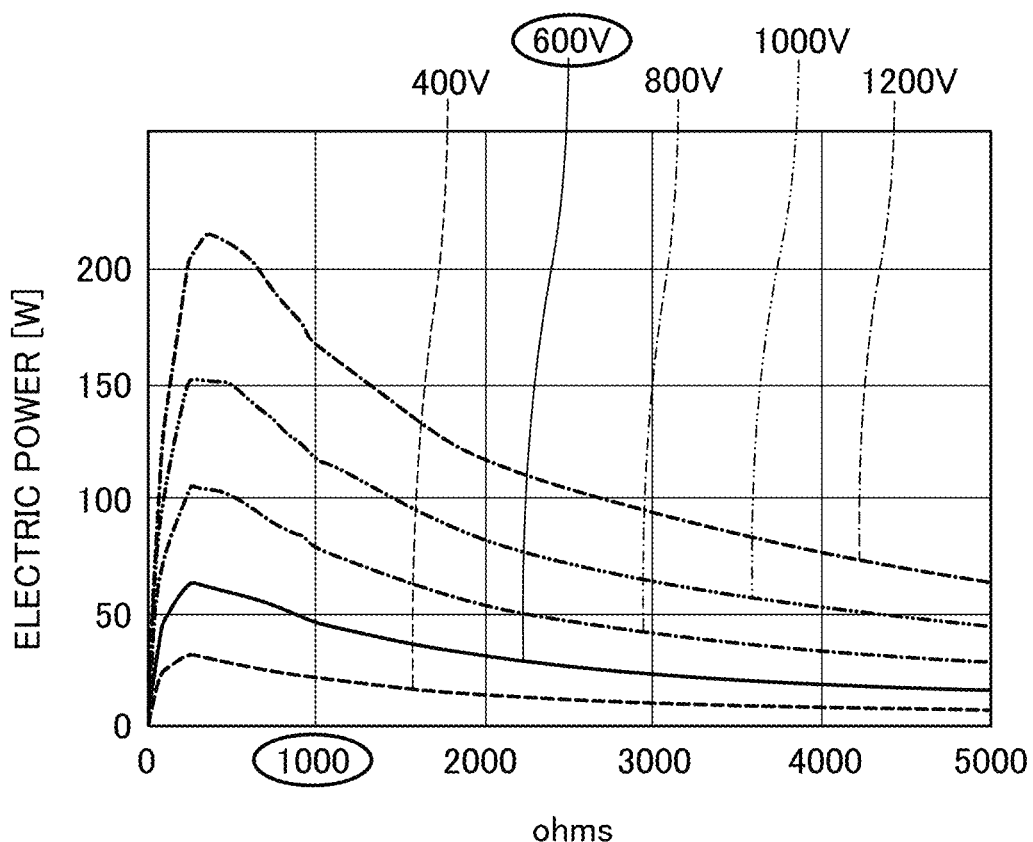
FIGS. 14A and 14B are explanatory diagrams presenting a result of a test on a discharge electric power.

FIGS. 14A and 14B are explanatory diagrams presenting a result of a test on a discharge electric power. In this test, c1 and c2 described below were determined while varying the "discharge voltage" of the discharge condition b1 to 400 V, 600 V, 800 V, 1000 V, and 1200 V. In this process, the discharge conditions b2 and b3 were set as described above (b2: 2 μs, b3: 200) and the pulse interval pi was set to 14 μs.

(c1) Size of the vapor layer VL to be formed. As the size of the vapor layer VL, a length of a part where the diameter of the vapor layer VL is largest in an image of the first electrode 11 photographed by a high-speed camera was measured.

(c2) Electric power value in varying a resistance load from 20 ohms to 5000 ohms. Each of the electric power values was determined by measuring a current flowing between the first electrode 11 and the second electrode 23 when a high frequency electric power was output from the RF generator 3 while a resistor (resistor of 20 ohms to 5000 ohms) was connected to between the first electrode 11 of the plasma guide wire 1 and the second electrode 23 of the catheter 2.

FIG. 14A presents a result of a test on the c1. FIG. 14A presents the size (mm) of the vapor layer VL for each voltage (V). As presented in FIG. 14A, the level of the voltage is proportional to the size of the vapor layer VL. Herein, based on the range of the pulse interval pi (3 μs or more and 25 μs or less) that provides the effectiveness examined in FIG. 13 and the result of the test on the size of the vapor layer in FIG. 7, the size of the vapor layer VL where the pulse interval pi is within a range that provides effectiveness is 0.75 mm or larger and 2.16 mm or smaller. The test result in FIG. 14A shows that, regarding the discharge voltage where the VL size is within the above range (range of the size of the vapor layer VL where the pulse interval pi is within the range that provides effectiveness), 400 V is too low, 800 V is too high, and 600 V is appropriate.

FIG. 14B presents a result of a test on the c2. In FIG. 14B, a curve indicating a relationship between the level of the resistance load and the electric power value is drawn for each voltage (V). In FIG. 14B, the ordinate represents the electric power value (W) determined by the test on the c2, and the abscissa represents the level (ohms) of the resistance load of the resistor used in the test on the c2. Resistances of living body tissues and body fluids are generally 1000 ohms or lower. From the result of the examination in FIG. 14A, the discharge voltage is suitably higher than 400 V and lower than 800 V, and therefore around 600 V. Thus, in FIG. 14B, referring to the curve (solid line) of 600 V discharge voltage where the resistance load is within a range of 1000 ohms or lower, the discharge electric power may be between 50 W or higher and 100 W or lower.

As described above, the results of each test described in FIGS. 7A to 14B show that, in the plasma ablation system 100 according to the first embodiment including the plasma guide wire 1 more flexible than conventional devices, the high frequency electric power output from the RF generator 3 is set to the discharge condition a1 or discharge condition a2 described above, so that the ablation effect can be obtained while suppressing flip-up on the distal end portion of the plasma guide wire 1.

As described above, the plasma ablation system 100 according to the first embodiment includes the plasma guide wire 1 including the conductive first electrode 11 formed on the distal end portion, and the catheter 2 including the conductive second electrode 23 formed on the distal end side. Thus, as a result of outputting the high frequency electric power to the first electrode 11 and the second electrode 23 while the plasma guide wire 1 is inserted through the catheter 2, the CTO 200 (living body tissue) can be ablated using an energy emitted by the discharge between the first electrode 11 and the second electrode 23. The RF generator 3 outputs a high frequency electric power that is 50 W or higher and 100 W or lower during discharge and pulse-modulated to have a duty ratio of 7.4% or higher and 40.0% or lower (discharge condition a1). Thus, for example, even when the first electrode 11 is disposed on the guide wire 1 more flexible (lower rigidity) than conventional configurations of a puncture device, a probe, a cutting electrode, a conductive blade, and the like, the vapor layer VL generated around the first electrode 11 during ablation can be minimized to suppress flip-up on the distal end portion of the guide wire 1 accompanying vibration of the surrounding substances. As a result, according to the first embodiment, safety can be improved in the plasma ablation system 100.

The RF generator 3 may output a high frequency electric power pulse-modulated so as to have a duty ratio of 9.1% or higher and 13.0% or lower (discharge condition a2). Thereby, the size and the depth of the hole formed by ablation can be made larger, while minimizing the vapor layer VL during ablation to suppress the flip-up on the distal end portion of the plasma guide wire 1.

Since the plasma guide wire 1 according to the first embodiment includes the conductive coil body 15 arranged to surround a part of the distal end side of the core shaft 14, the skin effect on the distal end side of the core shaft 14 can be reduced, and the distal end side of the core shaft 14 can be made thinner than the proximal end side. Since the plasma guide wire 1 includes the insulative covering portion 17 arranged to cover the outer periphery of the coil body 15, safety can be improved. As a result, the distal end side of the plasma guide wire 1 can be made more flexible, and safety of the plasma ablation system 100 can be improved.

Furthermore, since the plasma guide wire 1 according to the first embodiment has a distal end load of 0.3 gf or higher and 20.0 gf or lower, the distal end portion of the plasma guide wire 1 can be made flexible to improve safety. As a result, according to the first embodiment, the plasma guide wire 1 suitable for ablation using plasma stream can be provided.

Furthermore, the catheter 2 according to the first embodiment includes the connection portion 213 that electrically connects the second electrode 23 formed on the distal end side with the proximal end-side electrode 24 formed on the proximal end side and is embedded in the main body portion 211 (thicker wall portion) of the catheter 2. Thereby, it is possible to prevent obstruction of the operation due to the connection portion 213 entangled with the outer peripheral surface of the catheter 2 and prevent obstruction of the operation due to the connection portion 213 entangled with the plasma guide wire 1 inside the catheter 2, compared to a case where the connection portion 213 is exposed to the outside or inside of the catheter 2. As a result, the operability of the plasma ablation system 100 can be improved.

Second Embodiment

Figure 15:
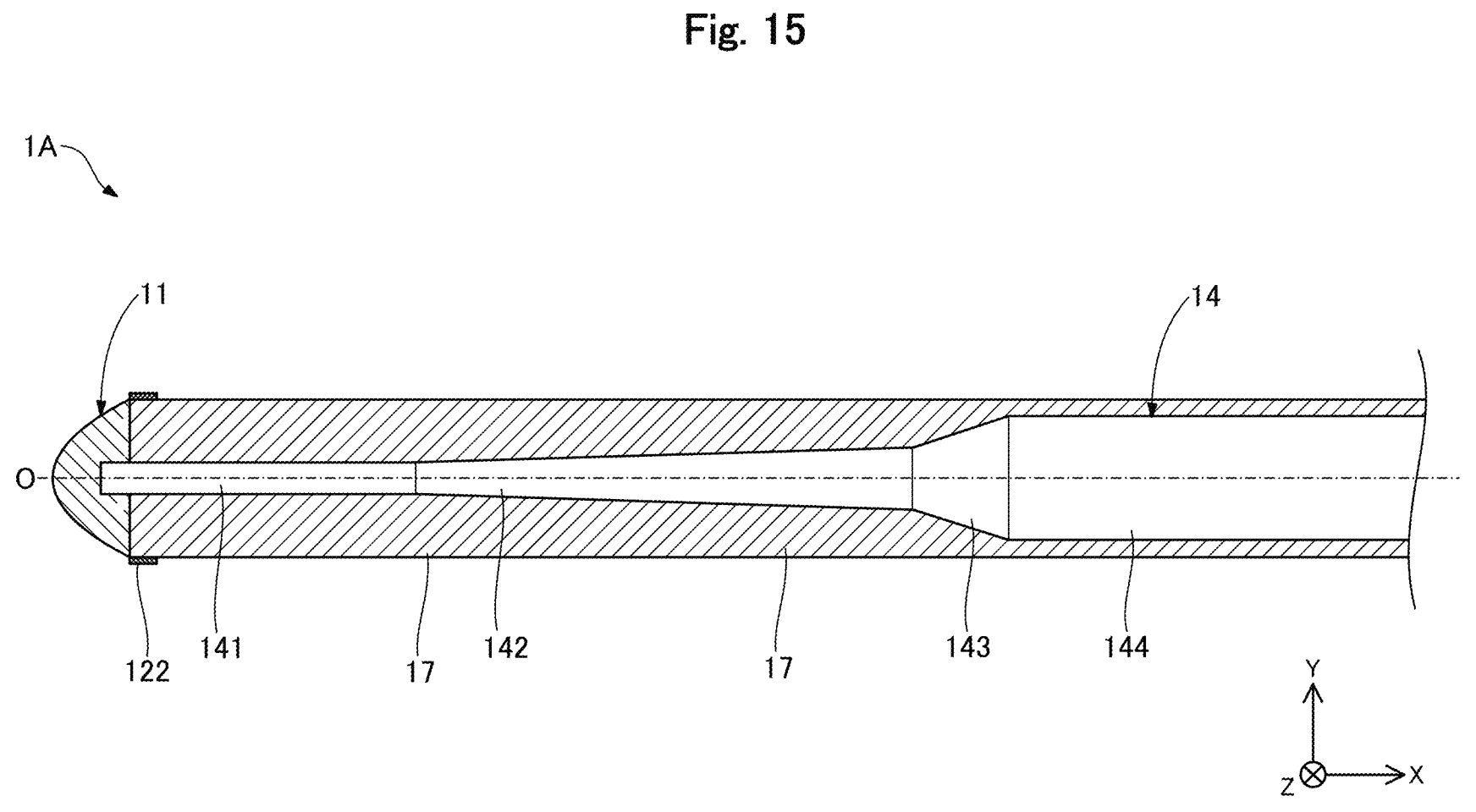

FIG. 15 is an explanatory diagram illustrating a cross-sectional configuration of a plasma guide wire 1A according to the second embodiment. The plasma ablation system 100 according to the second embodiment includes the plasma guide wire 1A illustrated in FIG. 15 instead of the plasma guide wire 1 described in the first embodiment. The plasma guide wire 1A does not include the coil body 15 and the fixation portion 152 described in the first embodiment.

Thus, the configuration of the plasma guide wire 1A can be variously modified, and the coil body 15 may be omitted. Also, the plasma ablation system 100 including this plasma guide wire 1A according to the second embodiment can exhibit a similar effect to the first embodiment. Since the plasma guide wire 1A according to the second embodiment does not have the coil body 15, the distal end side of the plasma guide wire 1A can be made thinner and the number of components constituting the plasma guide wire 1A can be decreased to reduce the number of steps and the cost for manufacturing the plasma guide wire 1A.

<Evaluation of Interelectrode Distance and Electrode Angle>

In the first embodiment, tests on the ablation effect were performed in FIGS. 8A to 10, and evaluation tests on the effectiveness of catching the guide wire were performed in FIGS. 11A to 12. In FIG. 13, the range of the pulse interval based on the results of these tests in FIGS. 8A to 12 was explained. Herein, for convenience, in the tests of FIGS. 8A to 10 (tests on the ablation effect) and the tests of FIGS. 11A to 12 (evaluation tests on effectiveness of catching the guide wire), the following conditions d1 and d2 were fixed as "distance L1: 10 mm, angle θ: 10 degrees". These conditions d1 and d2 will be evaluated below.

(d1) straight-line distance L1 between the first electrode 11 of the plasma guide wire 1 and the second electrode 23 of the catheter 2 (hereinafter also referred to as "interelectrode distance L1").

(d2) Angle θ between the central axis O of the catheter 2 and the surface 301 of the alternative model 300 (hereinafter also referred to as "electrode angle θ").

Figure 16:
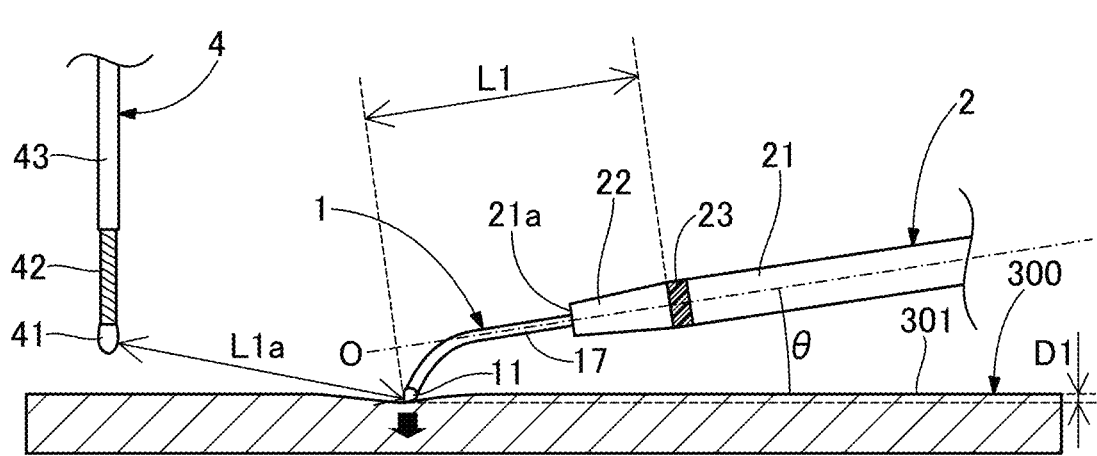
FIG. 16 is an explanatory diagram illustrating a method of a test on an interelectrode distance.

FIG. 16 is an explanatory diagram illustrating a method of a test on the interelectrode distance L1. First, the alternative model 300 of the living body tissue made of a urethane sponge and physiological saline simulating a body fluid are prepared, and the alterative model 300 is immersed in physiological saline. Then, as illustrated in FIG. 16, the first electrode 11 is brought into contact with the surface 301 of the alternative model 300 while the distal end side of the plasma guide wire 1 is protruded from the distal end opening 21a of the catheter 2. In this process, the first electrode 11 is brought into contact with the surface 301 such that a pushing depth D1 of the first electrode 11 against the surface 301 of the sample 300 is 1 mm. The pushing depth D1 means a difference in height between the surface 301 in the vicinity of the end portion of the alternative model 300 to which no force is applied from the first electrode 11 and the surface 301 of a part of the alternative model 300 which the first electrode 11 is in contact with, as illustrated in FIG. 16. Also in this experiment, an angle between the central axis O of the catheter 2 and the surface 301 of the alternative model 300 (electrode angle θ) was set to 10 degrees, and the distal end side of the plasma guide wire 1 was preshaped. The distal end load of the plasma guide wire 1 was set to 3.5 gf.

In this experiment, a return electrode 41 of a return wire 4 was used instead of the second electrode 23 of the catheter 2. The plasma guide wire 1 according to the second embodiment is flexible with a distal end load of 0.3 gf or higher and 20.0 gf or lower, as described above. Thus, if the distance L1 between the first electrode 11 and the second electrode 23 illustrated in FIG. 16 is directly changed for evaluation, a supporting force (improved rigidity) applied by the catheter 2 may affect the evaluation result. Thus, in this test, the evaluation was conducted using the return electrode 41 of the return wire 4 instead of the second electrode 23 of the catheter 2.

In the return wire 4, the conductive return electrode 41 is disposed on a distal end portion of a conductive coil body 42. A proximal end side of the coil body 42 is covered with a covering portion 43 made of an insulative resin. In this test, the evaluation was performed assuming that a straight-line distance L1a between the first electrode 11 of the plasma guide wire 1 and the return electrode 41 of the return wire 4 is the same as the straight-line distance L1 between the first electrode 11 of the plasma guide wire 1 and the second electrode 23 of the catheter 2 (i.e. the interelectrode distance L1). Specifically, each of the holes 302 formed on the alternative model 300 was examined by outputting a high frequency electric power of 200 pulses 60 times from the RF generator 3 while varying the straight-line distance L1a between the first electrode 11 and the return electrode 41, under the aforementioned discharge conditions b1 to b3.

Figure 17A:
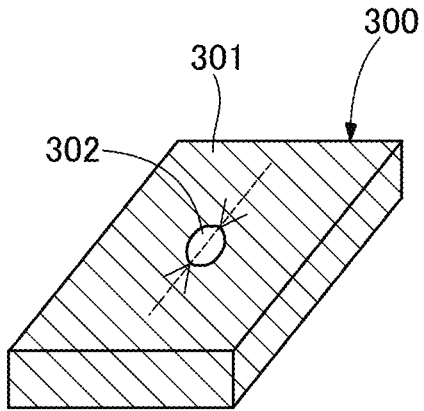
FIGS. 17A and 17B are diagrams illustrating a method for measuring a depth of a hole.
Figure 17B:
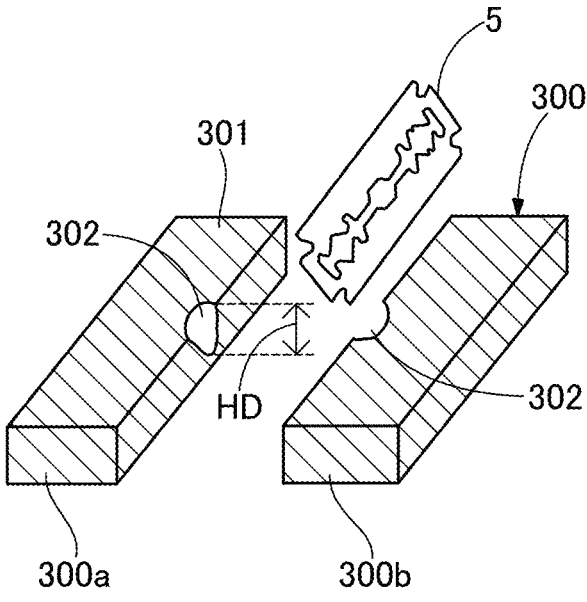

FIGS. 17A and 17B are diagrams illustrating a method for measuring the depth HD of the hole 302. FIG. 17A illustrates the alternative model 300 having the hole 302. FIG. 17B illustrates a state that the alternative model 300 is cut, e.g., by a blade 5. The depth HD of the hole 302 is measured as follows. First, as illustrated in FIG. 17A, the alternative model 300 having the hole 302 is cut along the longitudinal direction of the hole 302 using a feather cutter 5. Subsequently, a cross-section of one of a cut piece 300a or 300b of the alternative model 300 is photographed using a digital microscope to obtain a cross-sectional image. The obtained cross-sectional image is analyzed using a well-known image processing software (e.g., ImageJ) to measure the depth HD of the hole 302. The hole 302 formed in the alternative model 300 by ablation is not necessarily formed most deeply in a direction perpendicular to the surface 301 of the alternative model 300, but may be formed most deeply in a direction inclined to the surface 301 of the alternative model 300. The above measurement method makes it possible to accurately measure depths HD not only of the hole 302 perpendicular to the surface 301 of the alternative model 300 but also of the hole 302 inclined to the surface 301 of the alternative model 300.

Note that, the tests in FIGS. 8A to 10 (test on the ablation effect) and the tests in FIG. 11A to 12 (evaluation test on the catching effectiveness) were conducted in the same conditions, in which the pushing depth D1 was 1 mm, the plasma guide wire 1 with the distal end load of 3.5 gf was used, the high frequency electric power of 200 pulses was output 60 times from the RF generator 3, and the same measurement method for the depth HD of the hole 302 was used.

Figure 18:
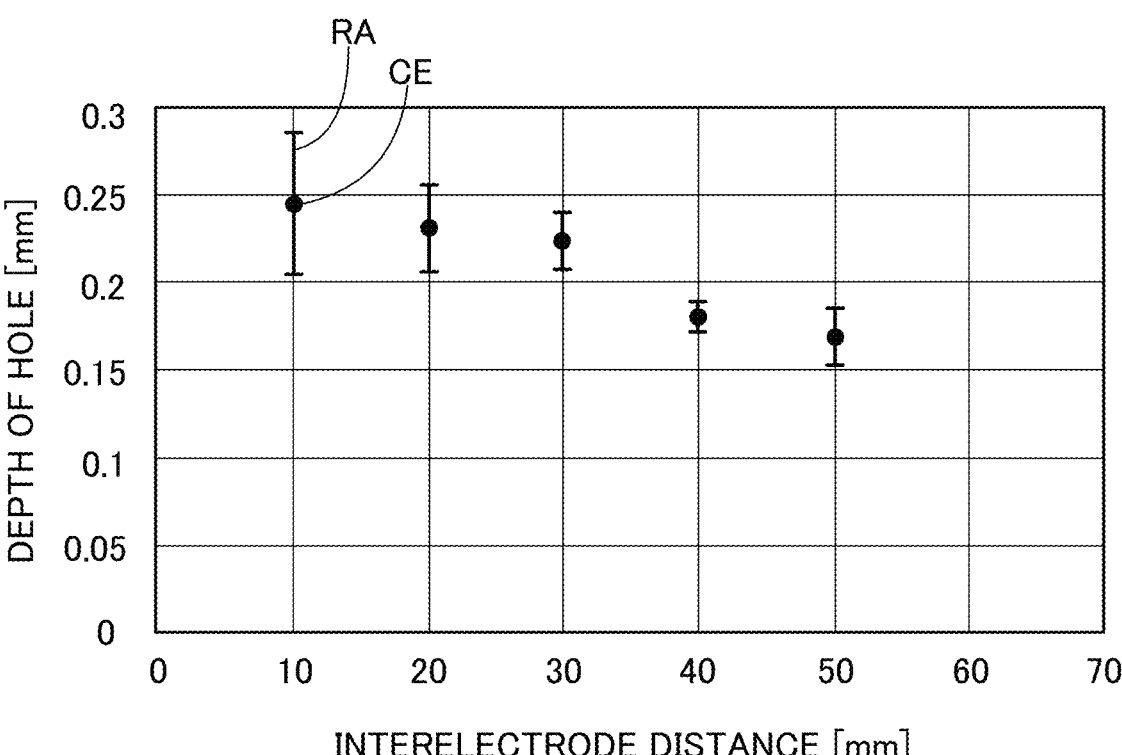
FIG. 18 is a graph presenting a result of the test on the interelectrode distance.

FIG. 18 is a graph presenting a result of the test on the interelectrode distance L1. In FIG. 18, the ordinate represents the depth (mm) of the hole 302, and the abscissa represents the interelectrode distance L1a (i.e., interelectrode distance L1). The bar RA in FIG. 18 represents a range of a standard deviation in the measurement result of the test performed multiple times (three times in this test) under the same condition, and the point CE represents a central point of the range of the standard deviation. The result in FIG. 18 shows that the interelectrode distance L1 of 10 mm or larger and 30 mm or smaller makes it possible to increase the depth HD of the hole 302. It can also be seen that a preferable depth HD can be obtained for the hoe 302, when the interelectrode distance L1 is 10 mm or larger and 50 mm or smaller, which is a range used in routine procedures. From the test result presented in FIG. 18, it is easy to predict that the depth HD of the hole 302 can be made deeper even when the interelectrode distance L1 is smaller than 10 mm. However, in the catheter 2 according to the second embodiment, the distal tip 22 having a length of about several millimeters in the direction of the central axis O is disposed on the more distal end side relative to the second electrode 23. Thus, it is difficult to assume that the interelectrode distance L1 is smaller than 10 mm, in light of the actual procedure in which ablation must be performed while recognizing that the first electrode 11 of the plasma guide wire 1 is definitely protruded from the distal tip 22 of the catheter 2 under X-ray fluoroscopy with poor visibility. On the other hand, in the actual procedure, both, rather than one, of the plasma guide wire 1 and the catheter 2 are advanced during ablation with plasma, and therefore it is difficult to assume that ablation is performed with the interelectrode distance L1 of longer than 50 mm.

Figure 19:
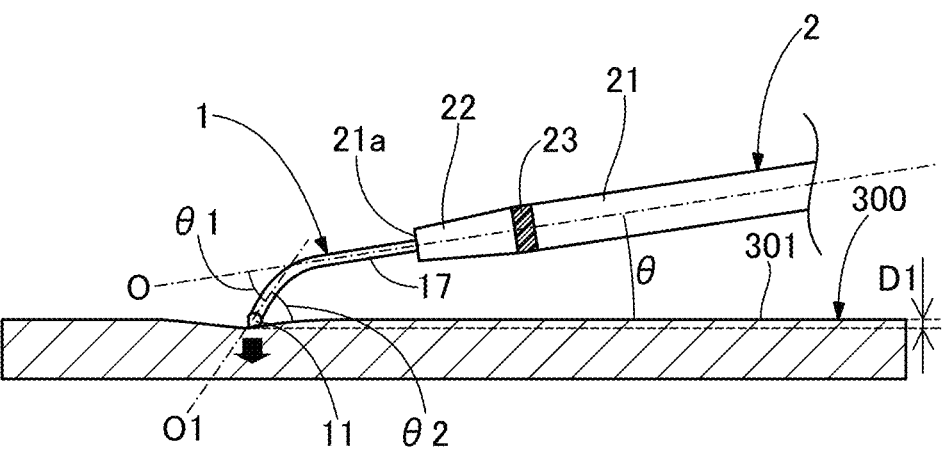
FIG. 19 is an explanatory diagram illustrating a method of a test on an electrode angle.

FIG. 19 is an explanatory diagram illustrating a method of a test on the electrode angle θ. First, the alternative model 300 of the living body tissue made of a urethane sponge and physiological saline simulating a body fluid are prepared, and the alternative model 300 is immersed in physiological saline. Then, as illustrated in FIG. 19, the first electrode 11 is brought into contact with the surface 301 of the alternative model 300 such that the pushing depth D1 is 1 mm while the distal end side of the plasma guide wire 1 is protruded from the distal end opening 21a of the catheter 2. In this experiment, the plasma guide wire 1 with a distal end load of 3.5 gf was used, the straight-line distance L1 (interelectrode distance L1) between the first electrode 11 of the plasma guide wire 1 and the second electrode 23 of the catheter 2 was set to 10 mm, and the distal end side of the plasma guide wire 1 was preshaped such that the angle between the distal end side and the surface 301 was 45 degrees. A preshaped angle θ1 is an angle between the central axis O of the catheter 2 and the central axis O1 of the distal end portion of the plasma guide wire 1, as illustrated in FIG. 19.

In this state, each hole formed on the alternative model 300 was examined by outputting a high frequency electric power of 200 pulses 60 times from the RF generator 3 while varying the angle θ (electrode angle θ) between the central axis O of the catheter 2 and the surface 301 of the alternative model 300 under the aforementioned discharge conditions b1 to b3. As a method for measuring the depth of the hole, the method described in FIGS. 17A and 17B was used.

Figure 20:
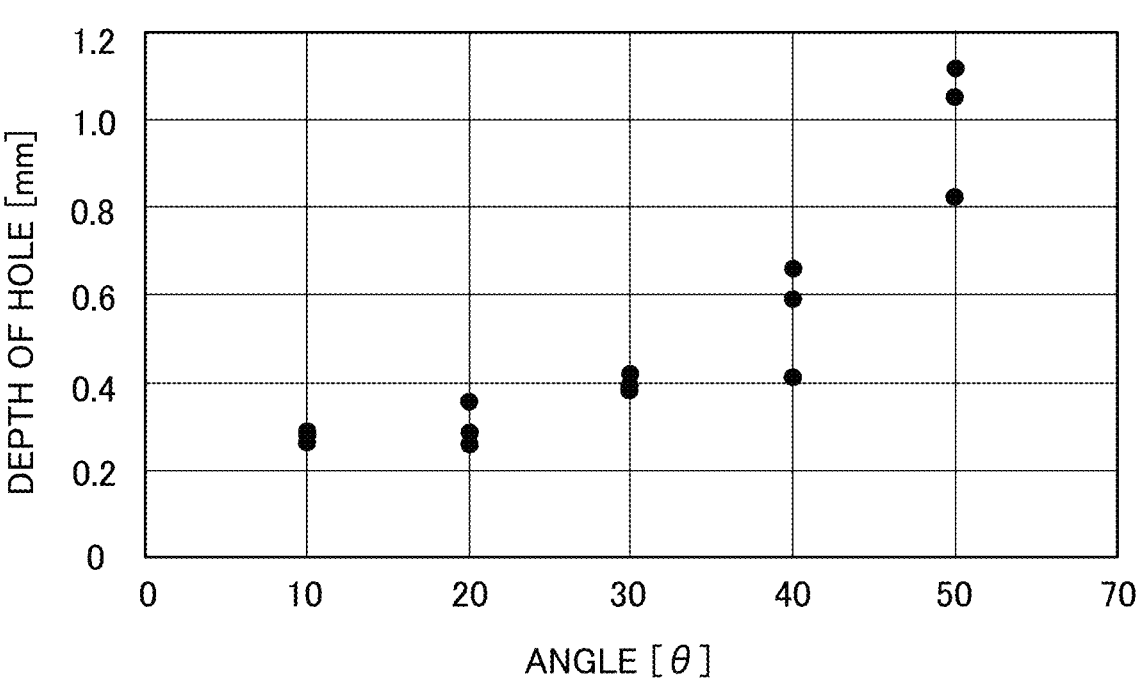
FIG. 20 is a graph presenting a result of the test on the electrode angle.

FIG. 20 is a graph illustrating a result of the test on the electrode angle θ. In FIG. 20, the ordinate represents the depth (mm) of the hole and the abscissa represents the electrode angle θ. In FIG. 20, results obtained from three tests under the same condition are each plotted with black circles. The result in FIG. 20 shows that the larger the electrode angle θ is, the larger the depth of the hole is, but a preferable hole depth can be obtained when the θ is 10 degrees or larger and 50 degrees or smaller, which is a range of the electrode angle θ used in routine procedures. It is difficult to assume that the electrode angle θ is set to smaller than 10 degrees, considering that the plasma guide wire 1 and the catheter 2 are used in a blood vessel. Also, it is difficult to assume that the electrode angle θ is set to larger than 50 degrees, considering that the distal end of the plasma guide wire 1 is generally preshaped.

As described above, the results of the tests in FIGS. 16 to 18 (tests on the interelectrode distance L1) showed that, in the range of the interelectrode distance L1 used in routine procedures, a preferable effect could be obtained by setting the discharge condition for the RF generator 3 to the discharge condition a1 or the discharge condition a2 described in the first embodiment. Specifically, when the straight-line distance L1 (interelectrode distance L1) between the first electrode 11 of the plasma guide wire 1 and the second electrode 23 of the catheter 2 is set to 10 mm or longer and 50 mm or shorter, the depth of the hole formed in the living body tissue by ablation using the plasma guide wire 1 can be within a desirable range.

The results of the tests in FIGS. 19 and 20 (tests on the electrode angle θ) showed that, in the range of the electrode angle θ used in routine procedures, a desirable effect could be obtained by setting the discharge condition for the RF generator 3 to the discharge condition a1 or the discharge condition a2 described in the first embodiment. Herein, as described above, since the plasma guide wire 1 according to the first and second embodiments has the preshaped distal end portion, an angle θ2 between the distal and portion of the plasma guide wire 1 and the living body tissue (in the example of FIG. 19, the alternative model 300) can be increased compared to a case without preshaping, and therefore the same effect as obtained by increasing the electrode angle 9 can be obtained. As a result, a depth of a hole formed on the living body tissue by ablation can be within a desirable range. The angle θ2 between the distal end portion of the plasma guide wire 1 and the living body tissue refers to an acute angle between the central axis O1 of the distal end portion of the plasma guide wire 1 and the surface of the living body tissue (in the example of FIG. 19, the surface 301 of the alternative model 300), as illustrated in FIG. 19.

Modification Examples of Embodiments

The disclosed embodiments are not limited to the embodiments described above and can be carried out in various aspects without departing from the spirit thereof and the following modifications are also possible, for example.

Modification Example 1

In each of the first and second embodiments, an example of the configuration of the plasma ablation system 100 was described. However, the configuration of the plasma ablation system 100 can be modified in various ways. For example, other devices may be used instead of the catheter 2, such as a pad having an electrode corresponding to the second electrode, and a guide wire having an electrode corresponding to the second electrode. For example, the plasma ablation system 100 may be composed of other input/output devices (e.g. foot switch, input/output touch panel, operating lever, operating button) and the like, not illustrated. For example, the plasma ablation system 100 may be composed other examination devices (e.g. computerized tomography (CT) device, magnetic resonance imaging (MI) device, X-ray imaging device, ultrasound imaging device, etc.) not illustrated.

Modification Example 2

An example of each configuration of the plasma guide wires 1 and 1A was described in the first and second embodiments above. However, the configuration of the plasma guide wire 1 can be modified in various ways. For example, the distal end load of the plasma guide wire 1 may be lower than 0.3 gf and higher than 20.0 gf. For example, the configuration of the core shaft 14 described above is merely an example, and at least a part of the small diameter portion 141, the first tapered portion 142, and the second tapered portion 143 may be omitted. For example, the shape of the first electrode 11 can be changed arbitrarily and can be any shape such as an arrowhead shape, a spherical shape, a columnar shape, and a polygonal columnar shape. For example, the distal end marker 122 and the proximal end-side electrode 24 may be omitted.

Modification Example 3

In the first and second embodiments, an example of the configuration of the catheter 2 was described. However, the configuration of the catheter 2 can be modified in various ways. For example, FIG. 1 illustrates, as the catheter 2, a so-called OTW type (over-the-wire type) catheter having openings on the distal and proximal ends of the shaft portion 21. However, the catheter 2 may be a so-called Rx type (rapid exchange type) catheter having a port (opening) for rapidly inserting and removing devices such as a delivery guide wire and the plasma guide wire 1. In this case, the port can be a through-hole that communicates between the outside and the inside of the lumen 21L at any position between the distal end and the proximal end of the shaft portion 21. The catheter 2 may be configured as a multi-lumen catheter including a plurality of lumens.

Modification Example 4

The configurations of the plasma guide wires 1 and 1A and the catheter 2 according to the first and second embodiments, and the configurations of the plasma guide wires 1 and 1A and the catheter 2 according to the modification examples 1 to 3 may be combined as appropriate.

Hereinbefore, the aspects of the disclosed embodiments have been described on the basis of the embodiments and modification examples, however, the embodiments of the aforementioned aspects are intended to facilitate understanding of the aspects and are not intended to limit the aspects. The aspects of the disclosed embodiments can be changed or modified without departing from the spirit thereof and the scope of claims, and also encompass equivalents thereof. In some instances, as would be apparent to one of skill in the art as of the filing of the present application, features, characteristics, and/or elements described in connection with a particular embodiment may be used singly or in combination with features, characteristics, and/or elements described in connection with other embodiments unless otherwise indicated. In addition, the aspects can be omitted as appropriate, unless technical features of the aspects are described as essential in the present specification.

No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

DESCRIPTION OF REFERENCE NUMERALS

1, 1A. Plasma guide wire
2. Catheter
3. RF generator
4. Return wire
5. Feather cutter
11. First electrode
14. Core shaft
15. Coil body
17. Covering portion
18. Connector
19. Cable
21. Shaft portion
22. Distal tip
23. Second electrode
24. Proximal end-side electrode
25. Cable
31. First terminal
32. Second terminal
33. First cable
34. First cable connector
35. Second cable
36. Second cable connector
41. Return electrode
42. Coil body
43. Covering portion
100. Plasma ablation system
122. Distal end marker
123. Covering layer
141. Small diameter portion
142. First tapered portion
143. Second tapered portion
144. Large diameter portion
151. Twisted wire
152. Fixation portion
200. CTO
201. Hole
211. Main body portion
212. Reinforcement portion
213. Connection portion
300. Alternative model
301. Surface
302. Hole

What is claimed is:

1. A plasma ablation system comprising:
a plasma guide wire having an elongated external shape and comprising a conductive first electrode formed on a distal end portion;
a catheter having an elongated external shape and comprising a conductive second electrode formed on a distal end side and a lumen through which the plasma guide wire is inserted; and
a radio frequency (RF) generator electrically connected to each of the plasma guide wire and the catheter to output a high frequency electric power to the first electrode and the second electrode, wherein the plasma guide wire can ablate a living body tissue by discharge between the first electrode and the second electrode, and the RF generator outputs the high frequency electric power that is between 50 W and 100 W, inclusive during discharge and pulse-modulated to have a duty ratio of between 7.4% and 40.0%, inclusive.

2. The plasma ablation system according to claim 1, wherein the RF generator outputs the high frequency electric power pulse-modulated to have a duty ratio of 9.1% or higher and 13.0% or lower.

3. The plasma ablation system according to claim 2, wherein the plasma guide wire has a distal end load of 0.3 gf or higher and 20.0 gf or lower.

4. The plasma ablation system according to claim 3, wherein the plasma guide wire includes, in addition to the first electrode, a conductive core shaft having an elongated external shape, a conductive coil body arranged to surround a part of a distal end side of the core shaft, and an insulative covering portion arranged to cover an outer periphery of the coil body, wherein the first electrode fixes each distal end of the core shaft, the coil body, and the covering portion.

5. The plasma ablation system according to claim 4, wherein the catheter includes, in addition to the second electrode, a conductive proximal end-side electrode formed on a proximal end side of the catheter and electrically connected to the RF generator, and a conductive connection portion that electrically connects the second electrode with the proximal end-side electrode and is embedded in a thicker wall portion of the catheter.

6. The plasma ablation system according to claim 5, wherein the catheter further comprises a mesh-shaped reinforcement portion made of mesh-woven strands and embedded in the thicker wall portion of the catheter.

7. The plasma ablation system according to claim 6, wherein a straight-line distance between the first electrode of the plasma guide wire and the second electrode of the catheter is 10 mm or longer and 50 mm or shorter.

8. The plasma ablation system according to claim 1, wherein the plasma guide wire has a distal end load of 0.3 gf or higher and 20.0 gf or lower.

9. The plasma ablation system according to claim 1, wherein the plasma guide wire includes, in addition to the first electrode, a conductive core shaft having an elongated external shape, a conductive coil body arranged to surround a part of a distal end side of the core shaft, and an insulative covering portion arranged to cover an outer periphery of the coil body, wherein the first electrode fixes each distal end of the core shaft, the coil body, and the covering portion.

10. The plasma ablation system according to claim 9, wherein the coil body is a multi-thread twisted wire coil formed by winding a plurality of twisted wires composed of a plurality of strands twisted together.

11. The plasma ablation system according to claim 1, wherein the catheter includes, in addition to the second electrode, a conductive proximal end-side electrode formed on a proximal end side of the catheter and electrically connected to the RF generator, and a conductive connection portion that electrically connects the second electrode with the proximal end-side electrode and is embedded in a thicker wall portion of the catheter.

12. The plasma ablation system according to claim 11, wherein the catheter further comprises a reinforcement portion embedded in the thicker wall portion of the catheter.

13. The plasma ablation system according to claim 12, wherein the reinforcement portion is made of mesh-woven strands.

14. The plasma ablation system according to claim 12, wherein the reinforcement portion includes a conductive material, and the thicker wall portion includes an insulating material between the reinforcement portion and the conductive connection portion.

15. The plasma ablation system according to claim 11, wherein the conductive connection portion has a coil shape made of conductive strands spirally wound along a circumferential direction of the catheter.

16. The plasma ablation system according to claim 12, wherein the reinforcement portion is closer to the lumen than the conductive connection portion.

17. The plasma ablation system according to claim 1, wherein a straight-line distance between the first electrode of the plasma guide wire and the second electrode of the catheter is 10 mm or longer and 50 mm or shorter.

18. The plasma ablation system according to claim 1, wherein the RF generator is further configured to output the high frequency electric power with a pulse width of 2 μs.

19. The plasma ablation system according to claim 1, wherein the plasma guide wire has a preshaped distal end portion.

20. The plasma ablation system according to claim 1, wherein the high frequency electric power is pulse-modulated with a pulse interval between 3 μs and 25 μs, inclusive.

* * * * *